United States Patent [19]

Siren et al.

[11] Patent Number: 5,278,332
[45] Date of Patent: Jan. 11, 1994

[54] DERIVATIVES OF CYCLOHEXANE

[75] Inventors: Matti Siren, Helsinki, Finland; Lars Perrson, Hassleholm, Sweden

[73] Assignee: Perstorp AB, Perstorp, Sweden

[21] Appl. No.: 926,153

[22] Filed: Aug. 5, 1992

Related U.S. Application Data

[63] Continuation-in-part of Ser. No. 458,904, Dec. 29, 1989, Pat. No. 5,157,140.

[51] Int. Cl.$^5$ ............................................... C07F 9/02
[52] U.S. Cl. ................................... 558/155; 558/156; 562/8; 546/12; 546/14; 548/452; 556/405
[58] Field of Search ................ 558/155, 156; 562/8; 546/12, 14; 548/452; 556/405

[56] References Cited

U.S. PATENT DOCUMENTS

| | | | |
|---|---|---|---|
| 4,777,134 | 10/1985 | Siren | 558/155 |
| 4,873,355 | 10/1989 | Hobbs | 558/161 |
| 5,157,140 | 10/1992 | Siren | 558/155 |

*Primary Examiner*—José G. Dees
*Assistant Examiner*—Samuel Barts
*Attorney, Agent, or Firm*—Scully, Scott, Murphy & Presser

[57] ABSTRACT

New derivatives of cyclohexane in substantially pure form suitable as pharmaceutical, foodstuff or as a stabilizer.

9 Claims, No Drawings

DERIVATIVES OF CYCLOHEXANE

CROSS REFERENCE TO RELATED APPLICATION

This is a continuation-in-part of U.S. patent application, Ser. No. 458,904 filed Dec. 29, 1989 now U.S. Pat. No. 5,157,140.

BACKGROUND OF THE DISCLOSURE

1. Field of the Invention

The present invention relates to novel derivatives of cyclohexane and compositions containing the same.

2. Background of the Prior Art

The family of isomeric hexahydroxy derivatives of cyclohexane are known as inositols. There exist nine different isomers and one of these, myo-inositol, is of biological importance. Chiro-inositols and scyllo-inositols are also of natural occurrence, but nothing is known of their biological role.

Myo-inositol is an essential nutrient for microorganisms and under special dietary condition for different animals.

There are some known derivatives of myo-inositol, such as phosphates and phospholipids.

Myo-inositol is found in plants principally as its hexaphosphate-ester, called phytic acid. It is further known that derivatives with a lower number of phosphate groups are formed during germination. The final products of the germination are myoinositol and inorganic phosphate.

One specific isomer of myo-inositoltriphosphate i.e. D-myo-inositol-1.4.5-triphosphate has been reported in Biochem. Biophys. Res. Commun. 120.2 (1984) p. 481. This compound is known as an intracellular calcium mobilizer in mammalian cells.

Other specific isomers of myo-inositoltriphosphate have been disclosed in the Swedish patent appln. No. 8504968-2.

Phospholipids are components of cell membranes. One type of phospholipis is the phosphoinositides in which myo-inositol is covalently linked to derivatives of glycerol.

Some methyl ethers of myo-inositol occur in plants. The most common one is the 5-methyl ether called seqnoyitol.

SUMMARY OF THE INVENTION

According to the present invention, it has quite unexpectedly been possible to produce novel derivatives of cyclohexane in substantially pure form.

DETAILED DESCRIPTION OF PREFERRED EMBODIMENTS

According to the invention, derivatives of cyclohexane of the structural formula (I)

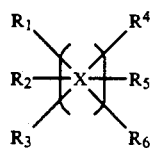

I have been produced in either acid or ester or salt form with high purity, wherein:

$R_1$, $R_2$ and $R_3$ independently are (a) hydrogen (b) oxygen (c) A, where A is
  (1) straight or branched alkyl with 1 to 24 carbon atoms, such as methyl, ethyl, propyl, butyl, pentyl, hexyl, heptyl, octyl, nonyl, decyl, dodecyl, tetradecyl, pentadecyl, hexadecyl, heptadecyl, octadecyl, eicosyl and docosyl;
  (2) cycloalkyl with 3 to 16 carbon atoms, such as cyclopropyl, cyclopentyl and cyclohexyl;
  (3) alkenyl with 2 to 24 carbon atoms, such as vinyl, allyl, propenyl, octadienyl, octenyl, decenyl, dodecenyl, tetradecenyl, hexadecenyl, octadecenyl, octadecadienyl, nonadecenyl, octadecatrienyl andarachiodonyl;
  (4) cycloalkenyl with 4 to 16 carbon atoms, such as cyclopentenyl, cyclopentadienyl, cyclohexenyl and cyclohexadienyl;
  (5) aryl with 6 to 24 carbon atoms, such as phenyl, biphenyl, terphenyl, naphtyl, anthracenyl and phenanthrenyl;
  (6) aralkyl, alkaryl, aralkenyl, alkenylaryl, wherein alkyl, aryl and alkenyl are as previously defined;
  (7) heterocyclic group containing at least one atom selected from the group of oxygen, nitrogen and sulphur, such as pyridyl, furyl and thiazolyl.

The above groups (1) to (7) are unsubstituted or substituted with hydroxy; oxo; alkoxy; aryloxy; halo; cyano; isocyanato; carboxy; esterified carboxy; amino; substituted amino; formyl; acyl; acyloxy; acylamino; sulfinyl, sulfonyl; phosphino; phosphinyl; phosphonyl; mercapto; alkylthio; arylthio; silyl; silyloxy; silylthio; nitro; azido; or the like.
(d) OB, where B is
  (1) A as defined previously
  (2) a glycosyl residue, such as glucose, mannose or glucosamine
  (3) a glycopeptide
  (4) a glycoprotein, such as lectins
  (5) a glycolipid, such as cerebroside
  (6) a halo, carboxy, phosphonyl, sulfonyl or the like.
(e)

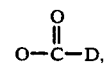

where D is
  (1) A as defined previously
  (2) carboxy or esterified carboxy
  (3) amino or substituted amino
(f) E, where E is
  (1) an amino acid, such as alanine, glycine, proline, methionine, serine, threonine or asparagine
  (2) a peptide, such as alanyl-alanyl, prolyl-methionyl or glycyl-glycyl
  (3) a protein including a lipoprotein and a nucleoprotein
(g) F, where F is
  (1) halo or haloformyl
  (2) carbonyl or substituted carbonyl
  (3) carbamyl or substituted carbamyl
  (4) carboxy or esterified carboxy
  (5) imino or amino or substituted imino or amino
  (6) mercapto or substituted mercapto
  (7) cyano or isocyanato
  (8) phosphino, phosphinyl or phosphonyl or substituted phosphino, phosphinyl or phosphonyl (9) sulfinyl or sulfonyl or substituted sulfinyl or sulfonyl
(10) silyl, silyloxy or silylthio
(11) nitro
(12) azido
(13) heterocyclic group containing at least one atom selected from the group of oxygen, nitrogen or sulphur
(14) xanthate or phosphorothioate
(15) hydroxyl where X is a radical of myo-inositol or a radical of a configuration isomer thereof and $R_4$, $R_5$ and $R_6$ independently are

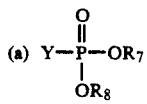

(a) $Y-\overset{\overset{O}{\|}}{\underset{\underset{OR_8}{|}}{P}}-OR_7$ where Y is
(1) oxygen or
(2) $(-CH_2-)_n$, where $n = 1-4$
(3) $(-CH_2-)_nO$, where $n = 1-4$ where $R_7$ and $R_8$ independently are
(1) hydrogen
(2) B as defined previously
(3) E as defined previously

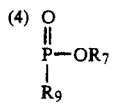

(4) $\overset{\overset{O}{\|}}{\underset{\underset{R_9}{|}}{P}}-OR_7$ where $R_7$ is defined previously and where $R_9$ is
(A) hydrogen
(B) hydroxyl
(C) B as defined previously
(D) OB, where B is defined previously
(E) E as defined previously
(F) amino or substituted amino
(5) -X as defined previously or phosphorylated X

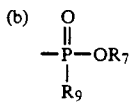

(b) $-\overset{\overset{O}{\|}}{\underset{\underset{R_9}{|}}{P}}-OR_7$ where $R_7$ and $R_9$ independently are as defined previously
(c) F as defined previously.

In Formula (I) $R_1$, $R_2$, $R_3$, $R_4$, $R_5$ and $R_6$ can be placed in any order to each other. The configuration isomers of myoinositol according to the invention are epi-, muco-, neo-, chiro-, scyllo-, allo- and cisinositol.

The intention of Formula (I) is not to cover compounds like inositol, inositoltriphosphate or phytic acid.

In the context of the present description, the general terms used above have the following meanings, radicals and compounds that are termed "lower" containing up to and including 7, preferably up to and including 4 carbon atoms:

Alkyl with 1 to 24 carbon atoms is for example, lower alkyl such as methyl, ethyl, n-propyl, isopropyl, n-butyl, tributyl, sec.-butyl or tert.-butyl, also n-pentyl, neopentyl, n-hexyl or n-heptyl or higher alkyl such as straight-chain or branched octyl, nonyl, decyl, undecyl, dodecyl, tridecyl, tetradecyl, pentadecyl, hexadecyl, heptadecyl, octadecyl, nonadecyl, eicosyl, docosyl and n-tetracosyl;

Cycloalkyl with 3 to 16 carbon atoms is, for example, cyclopropyl, cyclobutyl, cyclopentyl, cyclohexyl, cycloheptyl, cyclooctyl, cyclononyl and adamantyl;

Alkenyl with 2 to 24 carbon atoms is, for example, lower alkenyl such as vinyl, allyl, propenyl, butenyl, pentenyl and hexenyl or higher alkenyl such as octadienyl, octenyl, decenyl, dodecenyl, tetradecenyl, hexadecenyl, octadecenyl, octadecadienyl, octadecatrienyl, nonadecenyl and arachidonyl;

Cycloalkenyl with 4 to 16 carbon atoms is, for example, cyclobutenyl, cyclopentenyl, cyclohexenyl, cyclohexadienyl, cycloheptenyl, cyclooctenyl, cyclooctadienyl and cyclooctatrienyl;

Aryl with 6 to 24 carbon atoms is, for example, phenyl, biphenyl, terphenyl, naohtyl, anthracenyl, phenanthrenyl;

The radical A can also be a heterocyclic group containing at least one atom selected from the group of oxygen, nitrogen and sulphur and is for example pyridyl, pyrrolyl, pyrrolidinyl, piperidinyl, indolyl, imidazolyl, furyl, dioxolanyl, oxiranyl, thiiranyl, thiopyranyl, oxazolyl and thiazolyl.

The above mentioned radicals are unsubstituted or substituted.

The substitution could consist of free functional groups such as hydroxyl, carbonyl, carboxyl, mercapto or amino or these groups could be present in protected form.

Thus, carboxyl groups are usually protected in esterified form and contain as esterifying groups especially lower alkyl groups, which could be branched in the 1-position or suitably substituted in the 1- or 2-position. Preferred carboxyl groups protected in esterified form are inter alia methoxycarbonyl, butoxycarbonyl, tert. alkoxycarbonyl, for example tert. butoxycarbonyl, arylmethoxycarbonyl having one or two aryl radicals, these being especially phenyl radicals optionally substituted for example by lower alkyl, lower alkoxy, hydroxy, halogen and/or nitro, such as benzyloxycarbonyl, methoxybenzyloxycarbonyl, diphenylmethoxycarbonyl, 2-bromoethoxycarbonyl or 2-iodoethoxycarbonyl. Further preferred protected carboxyl groups in esterified form are silyloxycarbonyl groups, especially organic silyloxycarbonyl groups. In these the silicon atom contains as substituent preferably lower alkyl, especially methyl, also alkoxy, especially methoxy and/or halogen, for example chlorine. Suitable silyl-protecting groups are for example trimethylsilyl and dimethyltert.-butylsilyl.

A protected amino group may be, for example, in the form of an acylaminogroup or in the form of arylalkylamino group or azido group or sulphonated amino group. In a corresponding acylamino group acyl is for example the acyl radical of an organic carboxylic acid having for example up to 18 carbon atoms, especially of an alkanecarboxylic acid that is preferably substituted for example by halogen or aryl or of a carbonic acid semiester.

Such acyl groups are for example lower alkanoyl such as formyl or acetyl; halo-lower alkanoyl such as 2-chloro- and 2-bromoacetyl or lower alkoxycarbonyl straight or branched in the 1-position of the lower alkyl radical or suitably substituted in the 1- or 2-position, for example tert. butyl carbonyl; arylmethoxycarbonyl having one or two aryl radicals that are unsubstituted or, in the case of phenyl, may be substituted for example by lower alkyl, especially tert. lower alkyl, lower alkoxy, hydroxy, halogen and/or nitro; such as unsubstituted or substituted aryloxycarbonyl, for example benzyloxycarbonyl or 4-nitrobenzyloxycarbonyl or diphenylmethoxycarbonyl, for example benzhydroxycarbonyl or di-(4-methoxyphenyl)-methoxycarbonyl; aroylmethoxycarbonyl for example phenacyloxycarbonyl in which the aroyl group is benzoyl that is unsubstituted or substituted for example by halogen; halo-lower alkoxycarbonyl, for example 2-bromo- or 2-iodoethoxycarbonyl; or 2-(trisubstituted silyl)-ethoxycarbonyl such as for example 2-trimethylsilylethoxycarbonyl or 2-triphenylsilylethoxycarbonyl.

An arylalkylamino group is a mono-, di- or especially a triarylalkylamino group in which the aryl radicals are especially unsubstituted or substituted phenyl radicals. Such groups are for example benzylamino, diphenylmethylamino or tritylamino.

Amino groups may also contain organic silyl groups as protecting groups. Suitable silylprotecting groups are especially tri-lower alkylsilyl, such as trimethylsilyl and dimethyl-tert.-butylsilyl.

Preferred aminoprotecting groups are acyl radicals of carbonic acid semiesters especially tert.-butoxycarbonyl or aryloxycarbonyl that is unsubstituted or substituted for example benzyloxycarbonyl or 4-nitrobenzyloxycarbonyl or diphenylmethoxycarbonyl or 2.2.2-trichloroethoxycarbonyl.

Other protected amino groups are sulphonated amino groups such as lower alkyl sulphonamides especially N-methyl sulphonamide and N-butylsulphonamide.

Hydroxy- and mercapto-protecting groups are for example acyl radicals such as lower alkanoyl that is unsubstituted or substituted, for example by halogen, such as 2.2-dichloroacetyl or especially the acyl radicals of carbonic acid semiesters mentioned in connection with the amino-protecting groups and also etherifying groups such as tert.-butyl or 2-oxa- or 2-thia-aliphatic hydrocarbon radicals, for example 1-methoxyethyl, 1-methyl-thiomethyl or 2-oxa- or 2-thia-cycloaliphatic hydrocarbon radicals, for example 2-tetrahydrofuryl or 2-tetrahydropyranyl or corresponding thia analogues and unsubstituted or substituted benzyl, diphenylmethyl there coming into consideration as substituents of the phenyl radicals, for example halogen, lower alkoxy and/or nitro.

Hydroxy and mercapto groups may also be protected in the form of corresponding organic silyloxy or silylthio groups. Suitable silyl protecting groups are especially lower alkylsilyl such as trimethylsilyl or dimethyl-tert.-butyl-silyl.

Two free functional groups may also be substituted by a common protecting group. Thus, for example hydroxy groups may be substituted by a methylene radical that is unsubstituted or preferably substituted for example by lower alkyl, such as methyl or aryl, such as phenyl or such as methylene, isopropylidene, propylidene or benzylidene.

The substitutions on the radical A could also consist of a halogen especially fluorine, chlorine and iodine and further by a cyano group. The radical A could also be substituted with phosphorus containing radicals, such as phosphine, phosphinyl and phosphonyl and with nitrogen containing radicals such as nitro or azido.

The radical F can further be substituted with sulphur-containing groups such as sulphinyl or sulphonyl and siliconcontaining groups such as silyl, silyloxy or silylthio.

One or two or three of $R_1$, $R_2$ and $R_3$ can independently be etherified hydroxyl with the substitutent B. B can be A as defined previously, but preferably B is a straight or branched alkyl, especially a lower alkyl such as methyl, ethyl or butyl or a higher alkyl such as octyl, decyl, dodecyl or eicosyl or an alkenyl especially vinyl, allyl or butenyl. Preferably B can also be a cycloalkyl, especially cyclopropyl or cyclohexyl or a cycloalkenyl, especially cyclopentenyl or cyclooctadienyl.

In another preferred form, B is an aryl, especially phenyl, biphenyl and naphtyl. When the B radical is identical with the A radical it can be in unsubstituted or substituted form. The substitution could consist of free functional groups, such as hydroxyl, carbonyl, carboxyl, mercapto or amino or these groups could be present in protected form as described above. The substitution could also consist of halogen and phosphorus- and nitrogencontaining radicals.

Preferably, the substitution consists of hydroxy or repeated fragments of hydroxyl groups etherified with carbon radicals such as polyethyleneglycol and polypropyleneglycol. Other preferred substitution groups consist of a halogen, especially fluorine or chlorine or amino or protected aminogroups with carbon radicals especially alkoxycarbonyl such as methoxycarbonyl, butoxycarbonyl or aminocarbonyl or sulphur radicals such as methylsulphonyl or butylsulphonyl.

In another preferred form the substitution is mercapto or phosphine.

B can also be an etherified hydroxyl with a carbon radical which is a glycosyl residue. The glycosyl residue is derived for example from a monosaccharide such as erythrose, ribose, arabinose, allose, altrose, glucose, mannose, threose, xylose, lyxose, gulose, idose, galactose, talose, fructose or from a polysaccharide such as maltose, lactose, cellobiose or sucrose or nonhydrolyzed or partially hydrolyzed cellulose, amylose or amylopectin.

Preferably the glycosyl residue is derived from glucose, fructose, mannose or lactose.

The glycosyl residue could also be substituted with for example carboxyl, amino- or phosphonyl groups such as glucoseamine or galactoseamine or glucose-phosphate or glucopyranosyl phosphate or sialic acid.

B can also be an etherified hydroxyl with a carbon radical which is a glycopeptide. This radical is derived for example from one or more sugar residues which are attached primarily to serine, threonine or aspargine side chains of the peptide, where the peptide is formed by different combinations of amino acids up to a molecular weight of 10.000. Preferred radicals are those which include glucoseamine or galactoseamine attached to especially di- and tripeptides.

B can also be an etherified hydroxyl with a carbon radical which is a glycoprotein. This radical is derived for example from one or more sugar residues which are attached primarily to serine, threonine or aspargine side chains of the proteins, especially alkaline phosphatase, acetylcholinesterase, 5-nucleotidase, Thy-1, Th B and heparan sulphate proteoglycan. Preferred radicals are those which include glucoseamine and galactoseamine attached to the protein. Especially preferred radicals are lectins such as concanavalin A, wheat germ agglutinin, peanutagglutinin and seromucoid and orosomucoid.

B can also be an etherified hydroxyl with a carbon radical which is glycolipid. This radical is derived for example from one or more sugar residues which are attached to a lipid. Preferred radicals are those which include glucose or galactose. Further preferred radicals are cerebroside and ganglioside.

B can also be a halogen, especially fluorine and chlorine or a functional group such as carboxyl, phosphonyl or sulfonyl.

One or two or three of $R_1$, $R_2$ and $R_3$ can independently be esterified hydroxyl with the substituent D. D can be A as defined previously, but preferably the radical is derived from an organic carboxylic acid, especially an aliphatic, but also a cycloaliphatic, cycloaliphatic-aliphatic, aromatic or araliphatic carboxylic acid. Aliphatic carboxylic acids are inter alia alkane carboxylic acids that are unsubstituted or substituted for example by hydroxy or etherified or esterified hydroxy such as lower alkoxy or lower alkanoyloxy, by unsubstituted or substituted amino, such as lower alkylamino, di-lower alkylamino or by acylamino for example alkanoylamino and corresponding alkene- or alkyne carboxylic acids that may have one or more double or triple bonds. Preferably the radical is unsubstituted or hydroxysubstituted lower alkanecarboxylic acid such as acetic acid, butyric acid, caproic acid or 2-hydroxybutyric acid or unsubstituted or hydroxysubstituted higher alkanecarboxylic acid such as lauric acid or stearic acid. Preferably the radical is also a lower alkene- and lower alkyne-carboxylic acid such as acrylic acid or crotonic acid or higher alkene- and higher alkyne-carboxylic acid such as oleic acid and arachidonic acid.

In cycloaliphatic-aliphatic radicals the cycloaliphatic moiety and the aliphatic moiety have the meanings described above and are especially monocyclic or polycyclic cyclo-lower alkyl. Aromatic and araliphatic carboxy acids are inter alia benzoic or phenyl-lower alkanecarboxylic that are unsubstituted or substituted for example by alkyl, hydroxy, lower alkoxy or halogen. Preferably the radical is benzoic acid or phenolacetic acid.

D can also be an esterified hydroxy with a carbon-radical which is a carboxy group or esterified caboxy group to form a semiester or a diester. Preferred carboxygroups are lower alkane carboxyl such as acetoxy and butyryloxy. D can also be an esterified hydroxyl with a radical containing nitrogen such as amino or substituted amino. Preferably the radical is lower alkylamino for example methylamino, ethylamino and isopropylamino.

One or two or three of $R_1$, $R_2$ and $R_3$ can independently be esterified hydroxyl with the substituent E. E can be an amino acid, for example lysine, histidine, asparagine, arginine, aspartic acid, threonine, serine, glutamic acid, proline, glycine, alanine, cystine, valine, methionine, isoleucine, leucine, tyrosine, phenylalanine or tryptophan.

Preferably the amino acid is alanine, serine, glycine, threonine, methionine, asparagine and histidine.

E can also be a peptide consisting of the above mentioned amino acids up to a molecular weight of 10.000. Preferred radicals are dipeptides such as alanyl-alanyl, prolyl-methionyl, glycyl-glycyl or threonyl-histidyl.

E can be a protein such as albumin, antitrypsin, macroglobulin, haptoglobin, caeruloplasmin, transferrin, $\alpha$- or $\beta$-lipoprotein, $\beta$- or $\gamma$-globulin or fibrinogen.

One or more of $R_1$, $R_2$, $R_3$, $R_4$, $R_5$, $R_6$ can independently be the substituent F.

F can be a free functional group such as hydroxy, carbonyl, carboxyl, mercapto or amino or these could be protected with other groups as described for the radical A.

F can also be a halogen such as fluorine, chlorine, bromine and iodine and further a cyano or an isocyanato group.

F can also consist of phosphorus containing radicals such as phosphine, phosphinyl and phosphonyl or phosphorothioate and with nitrogen containing radicals such as nitro and azido.

F can further consist of sulphurcontaining radicals such as xanthate, sulfinyl or sulfonyl or siliconcontaining radicals such as silyl, silyloxy or silylthio.

F can also be a heterocyclic group containing at least one atom selected from the group of oxygen, nitrogen or sulphur.

F can further also be a carbamyl or substituted carbamyl.

When $R_1$, $R_2$ or $R_3$ are F the preferred radical is hydroxy, mercapto or halogen, especially fluorine and chlorine. Further preferred radicals are those where F is phosphino or amino or substituted amino. The substitution for the aminogroup is preferably a lower alkyl carbonyl radical such as methyl- or butylcarbonyl or sulphinyl or alkyl sulphinyl such as methylsulphinyl or butylsulphinyl or an aminocarbonyl such as N-methylaminocarbonyl.

When $R_4$, $R_5$ or $R_6$ are F the preferred radical is carboxy, carbamyl or substituted carbamyl, sulphonyl or substituted sulphonyl or phosphinyl or phosphonyl or substituted phosphinyl or phosphonyl. In this case F can also preferably be a heterocyclic group especially isoxazolyl, imidazolyl or thiazolyl.

One or two or three of $R_4$, $R_5$ and $R_6$ could independently be a phosphoruscontaining radical with the formula

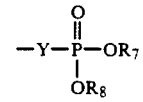

where Y is oxygen or $(-CH_2-)_n$ or $(-CH_2-)_n$ O; n=1-4.

In one preferred form Y is oxygen and especially preferred is when Y is oxygen and when $R_4$, $R_5$ and $R_6$ all have the above formula, i.e.

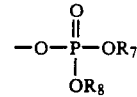

$R_7$ and $R_8$ can independently be hydrogen or B as defined previously. Preferably when $R_7$ and/or $R_8$ is B the radical is alkyl or aryl especially lower alkyl such as methyl, ethyl or butyl or higher alkyl such as octyl or dodecyl or aryl such as phenyl. In another preferred form B is substituted alkyl such as dihydroxy propyl or esterified dihydroxypropyl.

In another preferred form $R_7$ is hydrogen and $R_8$ is lower alkyl especially methyl, ethyl or butyl.

$R_7$ and $R_8$ can also be another phosphoruscontaining group with the formula

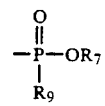

where $R_9$ is hydrogen, hydroxyl or B as defined previously. Preferably when $R_9$ is B the radical is alkyl or aryl especially lower alkyl such as methyl, ethyl or butyl or higher alkyl such as octyl or dodecyl or aryl such as phenyl. $R_9$ can also be an etherified hydroxyl with a radical B and preferably in this form B is alkyl or aryl as described above.

In one preferred form $R_4$, $R_5$, $R_6$ are a mono-or polyphosphate or alkylated or arylated mono- or polyphosphates.

$R_7$ and/or $R_8$ can also be a radical of myo-inositol or a radical of a configuration isomer thereof or a further phosphorylated radical of a configuration isomer of myo-inositol.

One or two or three of $R_4$, $R_5$, $R_6$ could independently be a phosphorus containing radical with the formula:

with $R_7$ and $R_9$ as defined previously.

In one preferred form $R_7$ is hydrogen and $R_9$ is amino or substituted amino such as alkylamino, especially methyl- or butylamino.

One embodiment of this invention relates to a compound of Formula (I), wherein $R_1$, $R_2$, $R_3$ independently are
a) F, where F is as defined previously or
b) hydrogen or oxygen or
c) A, where A is as defined previously,
wherein X is a radical of myo-inositol or a radical of a configuration isomer thereof and where $R_4$, $R_5$ and $R_6$ are as defined previously.

In this embodiment $R_1$ or preferably $R_1$ and $R_2$ are hydroxyl while $R_2$ and $R_3$ or preferably only $R_3$ are selected from the group of hydrogen, oxygen, F or A as defined previously.

Preferably, $R_2$ and $R_3$ or only $R_3$ are chlorine, bromine or iodine or most preferably fluorine. In another preferred form $R_2$ and $R_3$ or only $R_3$ are amino or substituted amino especially where the substitution on the aminogroup is a lower alkyl carbonyl radical such as methyl- or butylcarbonyl or sulphinyl or alkylsulphinyl radical such as methyl- or butylsulphinyl or an aminocarbonyl or a substituted aminocarbonyl such as N-methylaminocarbonyl.

In another preferred form $R_2$ and $R_3$ or only $R_3$ are unsubstituted or substituted mercapto, the substitution being preferably lower alkyl such as methyl- or butylmercapto.

In another form of this embodiment $R_2$ and $R_3$ or only $R_3$ are a phosphino, a xanthate or an isocyanatogroup. Other preferred forms are those where $R_2$ and $R_3$ or only $R_3$ are alkyl or aryl in unsubstituted or substituted form, especially lower alkyl such as ethyl and butyl and substituted ethyl and butyl with hydroxyl, mercapto, amino or phosphino or aryl such as phenyl.

In another preferred form $R_2$ and $R_3$ or only $R_3$ are hydrogen or oxygen.

In another preferred form of this invention $R_1$, $R_2$, $R_3$ are the same selected from
a) F, where F is as defined previously or
b) hydrogen or oxygen or
c) A, where A is as defined previously X is a radical of a configuration isomer of inositol and preferably a radical of myo-inositol.
$R_4$, $R_5$, $R_6$ are

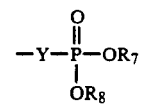

and/or F respectively, where Y, $R_7$, $R_8$ and F are as defined previously.

Preferably, $R_4$ and $R_5$ are

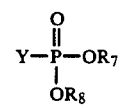

while $R_6$ is F.

Most preferably $R_4$, $R_5$ and $R_6$ are

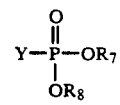

where Y is oxygen and $R_7$, $R_8$ are hydrogen or alkyl such as methyl, ethyl or butyl or aryl such as phenyl.

In this embodiment of the invention $R_1$, $R_2$, $R_3$ are the same and preferably hydrogen, oxygen, chlorine, bromine and iodine or most preferably fluorine.

In another preferred from $R_1$, $R_2$ and $R_3$ are amino or substituted amino especially where the substitution on the amino group is a lower alkylcarbonyl radical such as methyl- or butylcarbonyl or sulphinyl or alkylsulphinyl radical such as methyl- and butylsulphinyl or an aminocarbonyl or substituted aminocarbonyl such as N-methylaminocarbonyl.

In another preferred form $R_1$, $R_2$ and $R_3$ are unsubstituted or substituted mercapto, the substitution being preferably lower alkyl such as methyl- or butylmercapto.

In another form of this embodiment $R_1$, $R_2$ and $R_3$ are phosphino, xanthate or isocyanatogroups.

Other preferred forms are those where $R_1$, $R_2$ and $R_3$ are alkyl or aryl in unsubstituted form, especially lower alkyl such as ethyl and butyl or substituted ethyl and butyl with hydroxyl, mercapto, amino or phosphino or aryl such as phenyl.

The most preferred embodiment of this type of the invention is where $R_1$, $R_2$ and $R_3$ independently are covalently bound to $C_3$, $C_4$ and $C_5$ and where $R_4$, $R_5$ and $R_6$ independently are covalently bound to $C_1$, $C_2$ and $C_6$ in myo-inositol such as follows:

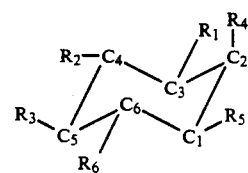

Other preferred embodiments of this invention are where $R_1$, $R_2$ and $R_3$ are independently bound to $C_4$, $C_5$ and $C_6$ and where $R_4$, $R_5$ and $R_6$ independently are covalently bound to $C_1$, $C_2$ and $C_3$ in myo-inositol such as follows:

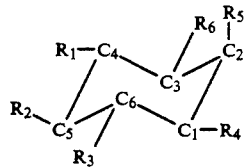

or where $R_1$, $R_2$ and $R_3$ are independently covalently bound to $C_2$, $C_5$ and $C_6$ and $R_4$, $R_5$ and $R_6$ independently are covalently bound to $C_1$, $C_3$ and $C_4$ in myo-inositol such as follows:

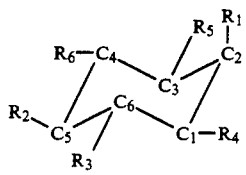

In one of the most preferred embodiments of this type of the invention $R_1$ and $R_2$ are hydroxyl and $R_3$ are as described above and $R_4$, $R_5$ and $R_6$ are

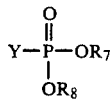

where Y is oxygen and $R_7$ and $R_8$ are hydrogen:

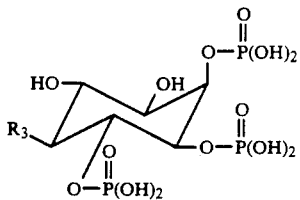

In this formula $R_3$ and the two hydroxyls could be in changed positions independently to each other. $R_3$ is especially selected from the group of hydrogen, oxygen, fluorine, chlorine, bromine and iodine and most preferably fluorine or selected from the group of amino or substituted amino especially where the substitution is a lower alkyl carbonyl radical such as methyl- or butyl-carbonyl or sulphinyl or alkylsulphinyl radical such as methyl- or butylsulphinyl or an aminocarbonyl or a substituted aminocarbonyl such as N-methylaminocarbonyl or selected from the group of unsubstituted or substituted mercapto, the substitution being preferably lower alkyl such as methyl-or butylmercapto or phosphino; or selected from the group of alkyl or aryl in unsubstituted form, especially lower alkyl such as ethyl and butyl or substituted ethyl or butyl with hydroxyl, mercapto, amino or phosphino or aryl such as phenyl.

In another form of this most preferred embodiment of this type of the invention $R_1$ and $R_2$ are hydroxyl and $R_3$ are as described above and $R_4$, $R_5$ $R_6$ are

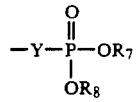

where Y is oxygen and where $R_7$, $R_8$ preferably are lower alkyl such as methyl and butyl:

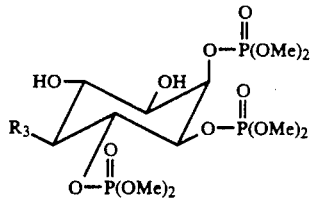

In another of the most preferred embodiments of this type of the invention $R_1$, $R_2$ and $R_3$ are the same and as described above and $R_4$, $R_5$, $R_6$ are

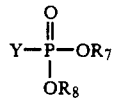

where Y is oxygen and $R_7$, $R_8$ are hydrogen:

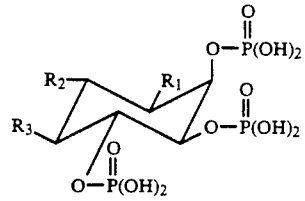

$R_1$, $R_2$, $R_3$ are especially selected from the group of hydrogen, oxygen, fluorine, chlorine, bromine and iodine and most preferably fluorine; or selected from the group of amino or substituted amino, especially where the substitution is a lower alkylcarbonyl radical such as methyl- or butylcarbonyl radicals or sulphinyl or alkylsulphinyl radical such as methyl- or butylsulphinyl or an aminocarbonyl or a substituted aminocarbonyl such as N-methyl aminocarbonyl or selected from the group of unsubstituted or substituted mercapto, the substitution being preferably lower alkyl such as methyl- or butyl mercapto or phosphino; or selected from the group of alkyl or aryl in unsubstituted from, especially lower alkyl such as ethyl and butyl or substituted ethyl or butyl with hydroxyl, mercapto, amino or phosphino or aryl such as phenyl.

In another form of this preferred embodiment of this type of the invention $R_1$, $R_2$ and $R_3$ are as described above and $R_4$, $R_5$ and $R_6$ are

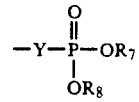

where Y is oxygen and where $R_7$ and $R_8$ preferably is lower alkyl such as methyl and butyl:

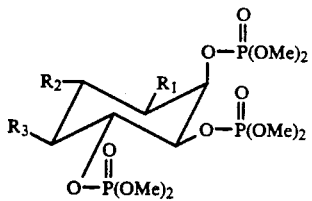

One embodiment of this invention relates to a compound of Formula (I) wherein $R_1$, $R_2$ and $R_3$ independently are:
a) hydroxyl or
b) OB, where B is as defined previously
wherein X is a radical of myo-inositol or a radical of a configuration isomer thereof and wherein $R_4$, $R_5$ and $R_6$ independently are as defined previously.

In this embodiment $R_1$ or preferably $R_1$ and $R_2$ are hydroxyl, while $R_2$ and $R_3$ or preferably only $R_3$ are etherified hydroxyl with the substituent B, where B is A as defined previously or a glycosyl residue, a glycopeptide, a glycoprotein, a glycolipid or selected from the group of halogen, carboxy, phosphonyl or sulphonyl. When B is A as defined previously, B is preferably a straight or branched alkyl, especially a lower alkyl such as methyl, ethyl or butyl or a higher alkyl such as octyl, dodecyl and eicosyl or an alkenyl, especially vinyl, alkyl or butenyl. Preferably, B can also be a cycloalkyl, especially cyclopropyl or cyclohexyl or aryl, especially phenyl, biphenyl or naphtyl. The above mentioned radicals can be unsubstituted or substituted especially with hydroxyl, mercapto, carboxyl, amino or phosphino.

By preference B can also be a glycosyl residue especially glucose, mannose, maltose, glucoseamine or glucosephosphate; or a glycopeptide especially a glycopeptide including glucoseamine or galactoseamine attached to di- and tripeptides such as alanyl-alanyl, prolyl-methionyl or glycyl-glycyl; or a glycoprotein, especially a glycoprotein including glucoseamine or galactoseamine attached to a protein such as concanavalin A, wheat germ agglutinin and peanutagglutinin; or a glycolipid especially a glycolipid including glucose or galactose such as cerebroside and ganglioside.

B can preferably also be halogen, especially fluorine or chlorine or carboxyl, phosphonyl or sulphinyl. In another preferred form the substitution OB are repeated fragments of hydroxyl groups etherified with carbon radicals such as polyethyleneglycol or polypropyleneglycol.

In another preferred form of this invention $R_1$, $R_2$ and $R_3$ are the same i.e. etherified hydroxyls with the carbon radical B as previously defined. X is a radical of a configuration isomer of inositol and preferably a radical of myo-inositol.

$R_4$, $R_5$ and $R_6$ are

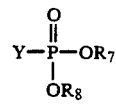

and/or F respectively, where Y, $R_7$, $R_8$ and F are as defined previously.

Preferably, $R_4$ and $R_5$ are

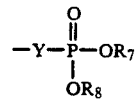

while $R_6$ is F.

Most preferably $R_4$, $R_5$ and $R_6$ are $$-Y-\overset{O}{\underset{OR_8}{\overset{\|}{P}}}-OR_7$$

where Y is oxygen and $R_7$ and $R_8$ are hydrogen or alkyl such as methyl, ethyl or butyl or aryl such as phenyl.

In this embodiment of the invention $R_1$, $R_2$ and $R_3$ are the same, that is etherified hydroxyl with the substituent B, which preferably is a straight or branched alkyl, especially a lower alkyl such as methyl, ethyl or butyl or a higher alkyl such as octyl, dodecyl or eicosyl or an alkenyl, especially vinyl, alkyl or butenyl. Preferably, B can also be a cycloalkyl, especially cyclopropyl or cyclohexyl or aryl, especially phenyl, biphenyl or naphtyl. The above mentioned radicals can be unsubstituted or substituted, especially with hydroxyl, mercapto, carboxyl, amino or phosphino.

By preference, B can also be a glycosyl residue, especially glucose, mannose, maltose, glucoseamine or glucosephosphate; or a glycopeptide, especially a glycopeptide including glucoseamine or galactoseamine attached to di- and tripeptides such as alanyl-alanyl, prolyl-methionyl or glycyl-glycyl; or a glycoprotein, especially a glycoprotein including glucoseamine or galactoseamine attached to a protein such as concanavalin A, wheat germ agglutinin and peanutagglutinin; or a glycolipid especially a glycolipid including glucose or galactose such as cerebroside and ganglioside.

B can preferably also be a halogen, especially fluorine or chlorine or carboxyl, phosphonyl or sulphinyl. In another preferred form the substitution OB are repeated fragments of hydroxyl groups etherified with carbon radicals such as polyethyleneglycol or polypropyleneglycol.

The most preferred embodiment of this type of the invention is where $R_1$, $R_2$ and $R_3$ independently are covalently bound to $C_3$, $C_4$ and $C_5$ and where $R_4$, $R_5$ and $R_6$ independently are covalently bound to $C_1$, $C_2$ and $C_6$ in myo-inositol such as follows:

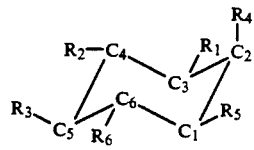

Other preferred embodiments of this invention are where $R_1$, $R_2$ and $R_3$ independently are covalently bound to $C_4$, $C_5$ and $C_6$ and where $R_4$, $R_5$ and $R_6$ independently are covalently bound to $C_1$, $C_2$ and $C_3$ in myo-inositol such as follows:

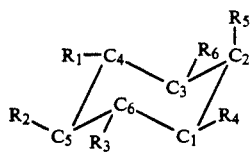

or where $R_1$, $R_2$ and $R_3$ independently are covalently bound to $C_2$, $C_5$ and $C_6$ and $R_4$, $R_5$ and $R_6$ independently are covalently bound to $C_1$, $C_3$ and $C_4$ in myo-inositol such as follows:

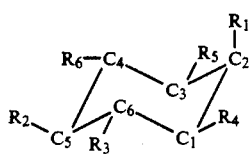

In one of the most preferred embodiments of this type of the invention $R_1$ and $R_2$ are hydroxyl and $R_3$ are as described above and $R_4$, $R_5$ and $R_6$ are

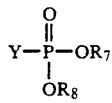

where Y is oxygen and $R_7$ and $R_8$ are hydrogen:

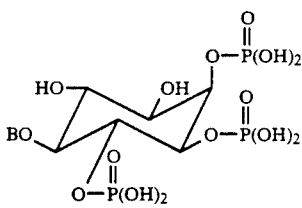

In this formula —OB and the two hydroxyls could be in changed positions independently to each other.

B is especially selected from the group of straight or branched alkyl such as methyl, butyl, dodecyl or eicosyl or alkenyl such as allyl or butenyl or cycloalkyl such as cyclopropyl or cyclohexyl or aryl such as phenyl unsubstituted or substituted especially with hydroxyl, mercapto, carboxyl, amino or phosphino; or selected from the group of a glycosyl residue especially glucose, mannose, glucoseamine or glucosephosphate or a glycopeptide especially including a glucoseamine or galactoseamine attached to a di- or tripeptide, or a glycoprotein especially including a glucoseamine or galactoseamine attached to the protein or a glycolipid including glucose or galactose; or selected from the group of halogen, especially fluorine or chlorine, or carboxy, phosphonyl or sulphinyl; or selected from the group consisting of repeated fragments of hydroxyl groups etherified with carbon radicals such as polyethyleneglycol or polypropyleneglycol.

In another form of this most preferred embodiment of this type of the invention $R_1$ and $R_2$ are hydroxyl and $R_3$ are described as above and $R_4$, $R_5$ and $R_6$ are

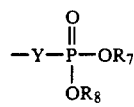

where Y is oxygen and where $R_7$ and $R_8$ preferably are lower alkyl such as methyl and butyl:

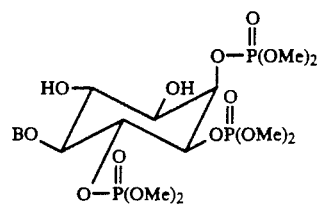

In another of the most preferred embodiments of this type of the invention $R_1$, $R_2$ and $R_3$ are the same and as described above and $R_4$, $R_5$ and $R_6$ are

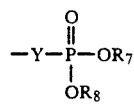

where Y is oxygen and $R_7$ and $R_8$ are hydrogen:

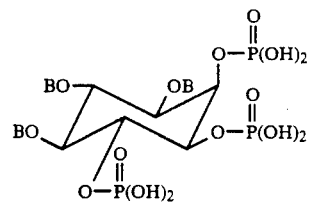

B is especially selected from the group of straight or branched alkyl, such as methyl, butyl, dodecyl or eicosyl or alkenyl such as allyl or butenyl or cycloalkyl such as cyclopropyl or cyclohexyl or aryl such as phenyl, unsubstituted or substituted especially with hydroxyl, mercapto, carboxyl, amino or phosphino; or selected from the group of a glycosyl residue especially glucose, mannose, glucoseamine or glucosephosphate or a glycopeptide especially including a glucoseamine or galactoseamine attached to a di- or tripeptide, or a glycoprotein especially including a glucoseamine or galactoseamine attached to the protein or a glycolipid including glucose or galactose, or selected from the group of halogen, especially fluorine or chlorine or carboxy, phosphonyl or sulphinyl; or selected from the group consisting of repeated fragments of hydroxyl groups etherified with carbon radicals such as polyethyleneglycol or polypropyleneglycol.

In another form of this most preferred embodiment of this type of the invention $R_1$, $R_2$ and $R_3$ are the same and as described above and $R_4$, $R_5$ and $R_6$ are

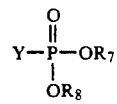

where Y is oxygen and where $R_7$ and $R_8$ preferably are lower alkyl such as methyl and butyl:

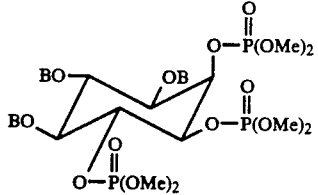

One embodiment of this invention relates to a compound of Formula (I) wherein $R_1$, $R_2$ and $R_3$ independently are
a) hydroxyl or

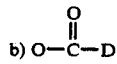

b) $O-\overset{\overset{O}{\|}}{C}-D$ where D is as defined previously or
c) E, where E is as defined previously,
wherein X is a radical of myo-inositol or a radical of a configuration isomer thereof and where $R_4$, $R_5$ and $R_6$ independently are as defined previously.

In this embodiment $R_1$ or preferably $R_1$ and $R_2$ are hydroxyl while $R_2$ and $R_3$ or preferably only $R_3$ are selected from the group of esterified hydroxyl with the substituents D or E, where D is A as defined previously, carboxy or esterified carboxy, amino or substituted amino and where E is an amino acid, peptide or a protein. When D is A as defined previously, D is preferably a radical derived from an organic carboxylic acid, especially an unsubstituted or substituted aliphatic acid such as acetic acid, butyric acid, caproic acid, lauric acid or 2-hydroxy butyric acid or an alkenic acid, such as acrylic acid or crotonic acid or an aromatic acid such as benzoic acid or phenylacetic acid.

By preference, D is also an esterified hydroxyl with a carbon radical which is a carboxy group or esterified carboxy group, especially acetoxy and butyryloxy-groups or a radical containing nitrogen such as amino or substituted amino, especially methyl-, ethyl- and isopropylamino. Preferably, E is an amino acid, especially asparginine, histidine, methionine and serine or a peptide consisting of amino acids up to a molecular weight of 10.000, especially dipeptides such as alanyl-alanyl, prolyl-methionyl and glycyl-glycyl or a protein, especially albumin, transferrin, α- and β-lipoprotein, β- and γ-globulin and fibrinogen.

In another preferred form of this invention $R_1$, $R_2$ and $R_3$ are the same selected from:

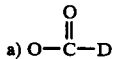

a) $O-\overset{\overset{O}{\|}}{C}-D$ where D is as defined previously or
b) E, where E is as defined previously
X is a radical of a configuration isomer of inositol and preferably a radical of myo-inositol.

$R_4$, $R_5$ and $R_6$ are

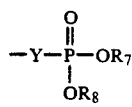

and/or F respectively, where Y, $R_7$, $R_8$ and F are as defined previously.

Preferably, $R_4$ and $R_5$ are

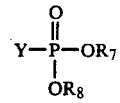

while $R_6$ is F.

Most preferably $R_4$, $R_5$ and $R_6$ are

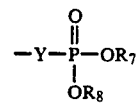

where Y is oxygen and $R_7$ and $R_8$ are hydrogen or alkyl, such as methyl, ethyl or butyl or aryl such as phenyl.

In this embodiment of the invention $R_1$, $R_2$ and $R_3$ are the same, that is esterified hydroxyl with the substituents D or E, where D preferably is a radical derived from an organic carboxylic acid, especially an unsubstituted or substituted aliphatic acid, such as acetic acid, butyric acid, caproic acid, lauric acid and 2-hydroxy butyric acid or an alkenic acid, such as acrylic acid or crotonic acid or an aromatic acid, such as benzoic acid or phenylacetic acid.

By preference, D is also an esterified hydroxyl with a carbon radical which is a carboxy group or esterified carboxy group, especially acetoxy and butyryloxy groups or a radical containing nitrogen, such as amino or substituted amino, especially methyl-, ethyl- and isopropylamino.

Preferably, E is an amino acid, especially asparagine, histidine, methionine and serine or a peptide consisting of amino acids up to a molecular weight of 10.000, especially dipeptides such as alanyl-alanyl, prolyl-methionyl and glycyl-glycyl or a protein, especially albumin, transferrin, α- and β-lipoprotein, β- and γ-globulin and fibrinogen.

The most preferred embodiment of this type of the invention is where $R_1$, $R_2$ and $R_3$ independently are covalently bound to $C_3$, $C_4$ and $C_5$ and where $R_4$, $R_5$ and $R_6$ independently are covalently bound to $C_1$, $C_2$ and $C_6$ in myo-inositol such as follows:

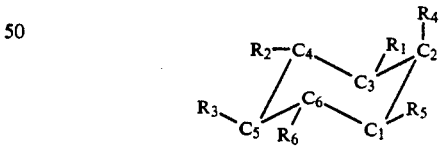

Other preferred embodiments of this invention are where $R_1$, $R_2$ and $R_3$ independently are covalently bound to $C_4$, $C_5$ and $C_6$ and where $R_4$, $R_5$ and $R_6$ independently are covalently bound to $C_1$, $C_2$ and $C_3$ in myo-inositol such as follows:

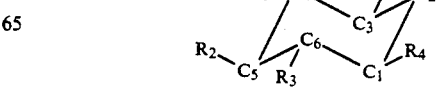

or where $R_1$, $R_2$ and $R_3$ independently are covalently bound to $C_2$, $C_5$ and $C_6$ and $R_4$, $R_5$ and $R_6$ independently are covalently bound to $C_1$, $C_3$ and $C_4$ in myo-inositol such as follows:

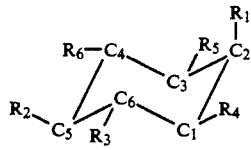

In one of the most preferred embodiments of this type of the invention $R_1$ and $R_2$ are hydroxyl and $R_3$ are as described above and $R_4$, $R_5$ and $R_6$ are

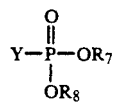

where Y is oxygen and $R_7$ and $R_8$ are hydrogen:

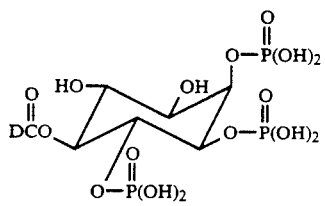

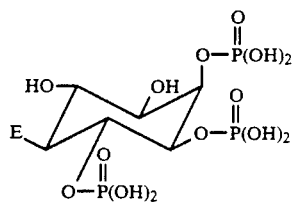

In this formula

or E and the two hydroxyls could be in changed positions independently to each other.

D is especially selected from the group of radicals derived from organic carboxylic acids such as acetic acid, butyric acid, lauric acid, 2-hydroxy butyric acid, acrylic acid and benzoic acid; or selected from the group of carboxy or esterified carboxy such as acetoxy and butyryloxy; or selected from the group of amino or substituted amino such as methyl- or isopropylamino.

E is especially selected from the group of amino acids, such as asparagine, histidine, methionine or serine or selected from the group of peptides such as alanyl-alanyl, or prolyl-methionyl or selected from the group of proteins, such as albumin, transferrin and α- and β-lipoprotein.

In another form of this most preferred embodiment of this type of the invention $R_1$ and $R_2$ are hydroxyl and $R_3$ are as described above and $R_4$, $R_5$ and $R_6$ are

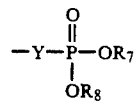

where Y is oxygen and where $R_7$ and $R_8$ preferably are lower alkyl such as methyl and butyl:

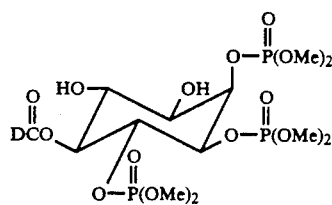

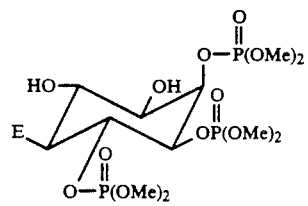

In another form of this most preferred embodiment of this type of the invention $R_1$, $R_2$ and $R_3$ are the same and as described above and $R_4$, $R_5$ and $R_6$ are

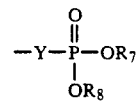

where Y is oxygen and $R_7$ and $R_8$ are hydrogen:

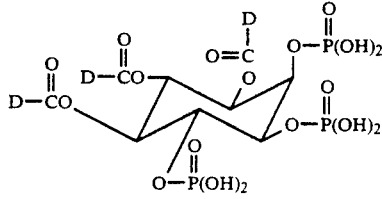

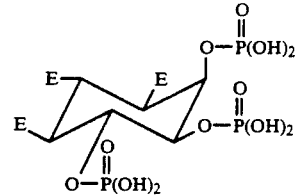

$R_1$, $R_2$ and $R_3$ are the same and are

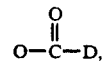

where D is especially selected from the group of radicals derived from organic carboxylic acids such as acetic acid, butyric acid, lauric acid, 2-hydroxybutyric acid, acrylic acid and benzoic acid; or selected from the group of carboxy or esterified carboxy, such as acetoxy and butyryloxy; or selected from the group of amino or substituted amino, such as methyl- or isopropylamino;

or E where E is especially selected from the group of amino acids, such as asparagine, histidine, methionine and serine; or selected from the group of peptides such as alanyl-alanyl or prolyl-methionyl or selected from the group of proteins such as albumin, transferrin and α- and β-lipoproteins.

In another from of this most preferred embodiment of this type of the invention $R_1$, $R_2$ and $R_3$ are the same and as described above and $R_4$, $R_5$ and $R_6$ are

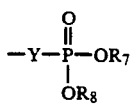

where Y is oxygen and where $R_7$ and $R_8$ preferably are lower alkyl such as methyl and butyl:

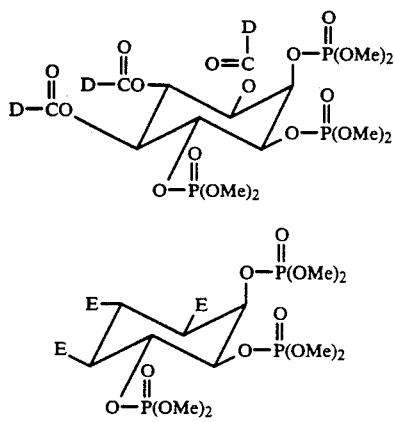

One embodiment of this invention relates to a compound of Formula (I), wherein $R_1$, $R_2$ and $R_3$ independently are as defined previously and where X is a radical of myo-inositol or a radical of a configuration isomer thereof and where $R_4$, $R_5$ and $R_6$ are

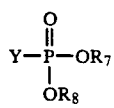

where Y, $R_7$ and $R_8$ are as defined previously.

Y is preferably oxygen and $R_7$ and $R_8$ are independently hydrogen or the radical B, especially unsubstituted alkyl such as methyl, ethyl, butyl, octyl or dodecyl or aryl such as phenyl or substituted alkyl such as dihydroxypropyl or esterified dihydroxypropyl; or E, especially an amino acid such as methionine or glycine.

In another preferred form $R_7$ and $R_8$ independently are another phosphorus containing group with the formula:

wherein $R_9$ is hydrogen, hydroxyl or B, especially selected from the group of alkyl such as methyl, ethyl, butyl, octyl or dodecyl or aryl such as phenyl or OB, especially methoxy, ethoxy, butoxy or phenoxy, or E, especially methionine or glycine, or X i.e. another configuration isomer of inositol or a phosphorylated configuration isomer of inositol or amino or substituted amino such as methyl- or butylamino.

In another preferred form of this embodiment $R_1$, $R_2$ and $R_3$ are as defined previously, X is a radical of myo-inositol or a radical of a configuration isomer thereof and $R_4$, $R_5$ and $R_6$ are

where $R_7$ and $R_9$ are as defined previously.

$R_7$ is preferably hydrogen or the radical B, especially unsubstituted alkyl such as methyl, ethyl, butyl, octyl or dodecyl or aryl such as phenyl or substituted alkyl such as dihydroxypropyl or esterified dihydroxypropyl or E, especially an amino acid such as methionine or glycine.

$R_9$ is preferably hydrogen, hydroxyl or B, especially selected from the group of alkyl such as methyl, ethyl, butyl, octyl, dodecyl or aryl such as phenyl or OB, especially methoxy, ethoxy, butoxy or phenoxy or E, especially methionine or glycine or X, i.e. another configuration isomer of inositol or a phosphorylated configuration isomer or amino or substituted amino such as methyl- or butylamino.

In another preferred form of this embodiment $R_1$, $R_2$ and $R_3$ are as defined previously, X is a radical of myo-inositol or a radical of a configuration isomer thereof and $R_4$, $R_5$ and $R_6$ are F, where F is as defined previously. F is preferably carboxyl or unsubstituted or substituted carbamyl, the substitution being preferably N-methyl-, N-propyl- or N-cyanocarbamyl or sulphonyl or substituted sulphonyl, especially aminosulphinyl or N-methyl- or N-butylaminosulphinyl. Other preferred forms of F are where F is phosphonyl or substituted phosphonyl such as aminophosphonyl or phosphorothioate. Preferably, F can also be a heterocyclic group, especially isoxazolyl, imidazolyl or thiazolyl.

In another preferred form of this invention $R_1$, $R_2$ and $R_3$ independently are as defined previously and X is a radical of a configuration isomer of inositol and preferably a radical of myo-inositol. $R_4$, $R_5$ and $R_6$ are

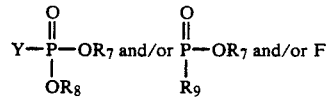

Preferably, $R_4$ and $R_5$ are

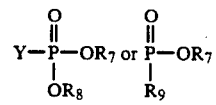

and $R_6$ is F, where Y, $R_7$, $R_8$, $R_9$ and F is as defined previously.

In this form Y is preferably oxygen and $R_7$ and $R_8$ are independently hydrogen or the radical B, especially unsubstituted alkyl such as methyl, ethyl, butyl, octyl or dodecyl or aryl such as phenyl or substituted alkyl such as dihydroxypropyl or esterified dihydroxypropyl; or E, especially an amino acid such as methionine or glycine. $R_9$ is preferably hydrogen, hydroxyl or the radical B, especially selected from the group of alkyl such as methyl, ethyl, butyl, octyl or dodecyl or aryl such as phenyl; or OB, especially methoxy, ethoxy, butoxy or phenoxy; or E, especially methionine or glycine or X i.e. another configuration isomer of inositol, preferably myo-inositol or a phosphorylated isomer of myo-inositol; or amino or substituted amino such as methyl- or butylamino.

F is preferably carboxyl; or unsubstituted or substituted carbamyl, especially N-methyl-, N-propyl- or N-cyanocarbamyl; or sulphonyl or substituted sulphonyl, especially aminosulphonyl or N-methyl- or N-butyl aminosulphonyl; or phosphonyl or substituted phosphonyl, especially aminophosphinyl; or a heterocyclic group, especially isoxazolyl, imidazolyl or thiazolyl.

The most preferred embodiment of this type of this type of the invention is where $R_1$, $R_2$ and $R_3$ independently are covalently bound to $C_3$, $C_4$ and $C_5$ and where $R_4$, $R_5$ and $R_6$ independently are covalently bound to $C_1$, $C_2$ and $C_6$ in myo-inositol such as follows:

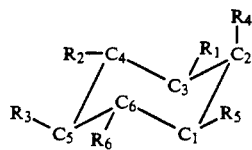

Other preferred forms of this invention are where $R_1$, $R_2$ and $R_3$ independently are covalently bound to $C_4$, $C_5$ and $C_6$ and where $R_4$, $R_5$ and $R_6$ independently are covalently bound to $C_1$, $C_2$ and $C_3$ in myo-inositol such as follows:

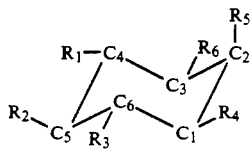

or where $R_1$, $R_2$ and $R_3$ independently are covalently bound to $C_2$, $C_5$ and $C_6$ and where $R_4$, $R_5$ and $R_6$ independently are covalently bound to $C_1$, $C_3$ and $C_4$ in myo-inositol such as follows:

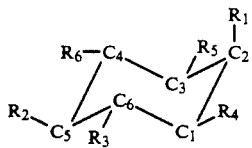

In one of the most preferred embodiments of this type of the invention $R_1$, $R_2$ and $R_3$ are hydroxyl and $R_4$, $R_5$ and $R_6$ are-

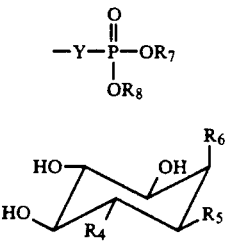

Preferably, Y is oxygen and $R_7$ and/or $R_8$ are hydrogen; or methyl, ethyl, butyl, octyl, dodecyl, phenyl, dihydroxypropyl or esterified dihydroxypropyl, especially with $C_{14}$ to $C_{20}$ alkylcarbonyl groups; or glycine, methionine or histidine.

In another of the most preferred embodiments of the invention $R_1$, $R_2$ and $R_3$ are hydroxyl and $R_4$, $R_5$ and $R_6$ are

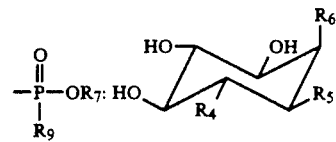

Preferably, $R_7$ is hydrogen; or methyl, ethyl, butyl, octyl, dodecyl, phenyl, dihydroxypropyl or esterified dihydroxypropyl with $C_{14}$ to $C_{20}$-alkylcarbonyl groups; or glycine, methionine or histidine and $R_9$ is preferably hydrogen or hydroxyl; or methyl, ethyl, butyl, octyl, dodecyl or phenyl; or methoxy, ethoxy, butoxy or phenoxy; or glycine or methionine; or another configuration isomer of myo-inositol or a phosphorylated isomer of myo-inositol; or amino, methyl- or butylamino.

In another of the most preferred embodiments of this invention $R_1$, $R_2$ and $R_3$ are hydroxyl and $R_4$, $R_5$ and $R_6$ are F:

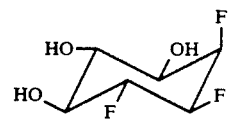

Preferably, F is carboxyl; or carbamyl, N-methylcarbamyl, N-propylcarbamyl or N-cyanocarbamyl; or sulphonyl, aminosulphonyl, N-methyl- or N-butylaminosulphonyl; or phosphonyl or aminophosphonyl; or isoxazolyl, imidazolyl or thiazolyl.

In another of the most preferred embodiments of this invention $R_1$, $R_2$ and $R_3$ are hydroxyl and $R_4$ and $R_5$ are

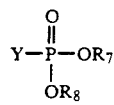

and $R_6$ is F.

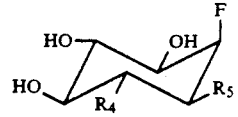

In this formula F and $R_4$ and $R_5$ could be in changed positions independently to each other.

Preferably, Y is oxygen and $R_7$ and/or $R_8$ are hydrogen or methyl, ethyl, butyl, octyl, dodecyl, phenyl, dihydroxypropyl or esterified dihydroxypropyl, especially with $C_{14}$ to $C_{20}$-alkyl carbonyl groups; or glycine, methionine or histidine, and F is hydroxyl or carboxyl; or carbamyl, N-methylcarbamyl, N-propylcarbamyl or N-cyanocarbamyl; or sulphonyl, aminosulphonyl, N-methyl- or N-butylaminosulphonyl; or phosphonyl or aminophosphonyl; or isoxazolyl, imidazolyl or thiazolyl.

In one preferred form $R_1$, $R_2$, $R_3$ and $R_6$ are hydroxyl and $R_4$ and $R_5$ are phosphate:

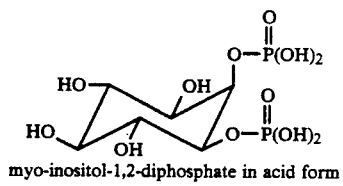
myo-inositol-1,2-diphosphate in acid form

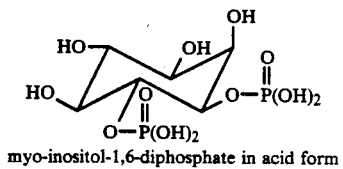
myo-inositol-1,6-diphosphate in acid form

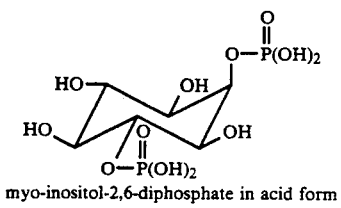
myo-inositol-2,6-diphosphate in acid form

These latter three described forms of the invention are pharmaceutically active towards conditions characterized by metal disturbance, free radical formation and cell membrane destabilization.

In one preferred form of this invention $R_1$ is OB and $R_2$ is hydroxyl or OB, $R_3$, $R_4$, $R_5$ are hydroxyl and $R_6$ are

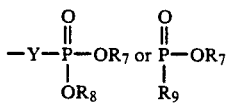

with the following formula:

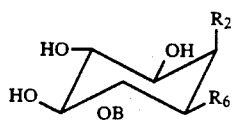

In this formula $R_2$, $R_6$ and OB could be in changed positions independently to each other.

Preferably Y is oxygen and $R_7$ and/or $R_8$ are hydrogen; or dodecyl or eicosyl; or esterified dihydroxypropyl, especially with $C_{14}$ to $C_{20}$ -alkylcarbonyl groups and $R_9$ is hydrogen, hydroxyl or amino or another configuration isomer of myo-inositol or a phosphorylated isomer of myo-inositol. Preferably, B is a glycosyl residue, especially glucose, mannose, glucosamine or a glycoprotein.

Of particular importance is the compound having the structural formula

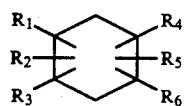
II where $R_1$, $R_2$ and $R_3$ are the same or different and are
(a) hydroxyl;

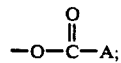 (b)

where A is
(1) straight or branched chain alkyl containing 1 to 24 carbon atoms,
(2) cycloalkyl containing 3 to 16 carbon atoms,
(3) alkenyl containing 3 to 24 carbon atoms,
(4) cycloalkenyl containing 5 to 16 carbon atoms,
(5) aryl containing 6 to 26 ring carbon atoms,
(6) aralkyl containing 7 to 48 carbon atoms,
(7) alkaryl containing 7 to 48 carbon atoms,
(8) aralkenyl containing 8 to 48 carbon atoms,
(9) alkenylaryl containing 8 to 48 carbon atoms,
(10) a heterocyclic ring containing at least one atom of oxygen, nitrogen or sulfur
said meanings (1) to (10) of A being unsubstituted or substituted with hydroxy, oxo, alkoxy, aryloxy, halo, cyano, isocyano, carboxy, carbalkoxy, carbaryloxy, amino, alkyl or aryl substituted amino, formyl, acyl, acyloxy, acylamino, sulfinyl, sylfonyl, phosphino, phosphinyl, phosphonyl, mercapto, alkylthio, arylthio, silyl, silyloxy, nitro or azido;
(11) carboxy,
(12) carbalkoxy,
(13) carbaryloxy,
(14) amino,
(15) alkyl substituted amino or
(16) aryl substituted amino;
(c) D, where D is
(1) an amino acid
(2) a peptide or
(3) a protein complex including a lypoprotein and a nucleoprotein;
(d) E, where E is
(1) carbamoyl,
(2) alkyl substituted carbamoyl,
(3) aryl substituted carbamoyl,
(4) sulfinyl,
(5) alkyl substituted sulfinyl,
(6) aryl substituted sulfinyl,
(7) sulfonyl,
(8) alkyl substituted sulfonyl,
(9) aryl substituted sulfonyl,
(10) xanthate or
(11) phosphorothioate;
and where $R_4$, $R_5$ and $R_6$ are the same or different and are (a) $O-\overset{\overset{O}{\|}}{\underset{OR_8}{P}}-OR_7$, wherein $R_7$ and $R_8$ are the same or different and are:
(1) hydrogen,
(2) A,
(3) a glycosyl residue,
(4) a glycopeptide,
(5) a glycoprotein,
(6) a glycolipid,
(7) halogen,
(8) carboxy,
(9) phosphonyl,
(10) sulfonyl,
(11) an amino acid,

(12) a peptide,
(13) a protein complex including a lipoprotein and a nucleoprotein,
(14) cyclohexyl,
(15) phosphate substituted cyclohexyl or

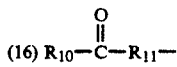

where $R_{10}$ is hydrogen, straight or branched chain alkyl containing 1 to 4 carbon atoms, amino, aryl, methylamino or dimethylamino; and $R_{11}$ is $-CH_2$, $-CHCH_3$ or $-C(CH_3)_2$ or (b) hydroxyl, with the proviso that if $R_1$, $R_2$ and $R_3$ are hydroxyl, at least one of $R_4$, $R_5$ and $R_6$ is

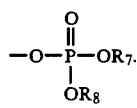

It is emphasized that acyl has the meaning

where R is alkyl or aryl; acyloxy has the meaning

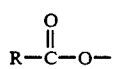

where R is alkyl or aryl; acylamino has the meaning

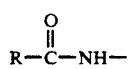

where R is alkyl or aryl. It is furthermore emphasized that acyloxyalkyl has the meaning

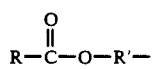

where R is alkyl or aryl and R' is alkyl.

In a first preferred set of embodiments $R_1$, $R_2$, $R_3$, $R_4$, $R_5$ and $R_6$ in the compound having the structural formula II, are either hydroxyl or

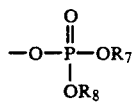

where $R_7$ is acyloxyalkyl; and $R_8$ is hydrogen or acyloxyalkyl. In one such preferred embodiment of this set of embodiments $R_1$, $R_2$ and $R_3$ are hydroxyl; and $R_4$, $R_5$ and $R_6$ are

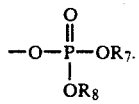

In another preferred embodiment of this set of embodiments $R_1$, $R_2$, $R_3$ and $R_4$ are hydroxyl; and $R_5$ and $R_6$ are

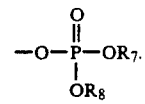

In a third preferred embodiment of this set of embodiments $R_1$, $R_2$, $R_3$, $R_4$ and $R_5$ are hydroxyl; and $R_6$ is

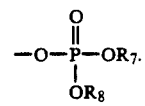

In another series of this set of preferred embodiments the meanings of $R_1$, $R_2$, $R_3$, $R_4$, $R_5$ and $R_6$ are identical with those given in the above paragraph. However, in this set of preferred embodiments the compounds have the structural formula

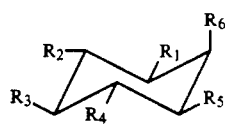

III

In another preferred set of embodiments the compound having the structural formula II is characterized by all the substituents, $R_1$, $R_2$, $R_3$, $R_4$, $R_5$ and $R_6$, being either hydroxyl or

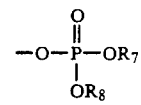

where $R_7$ is straight or branched chain alkyl containing 1 to 24 carbon atoms, cycloalkyl containing 3 to 16 carbon atoms or aryl containing 6 to 26 ring carbon atoms; and $R_8$ is hydrogen, straight or branched chain alkyl containing 1 to 24 carbon atoms, cycloalkyl containing 3 to 16 carbon atoms or aryl containing 6 to 26 ring carbon atoms.

In one such preferred embodiment of this preferred set of embodiments $R_1$, $R_2$ and $R_3$ are hydroxyl; and $R_4$, $R_5$ and $R_6$ are

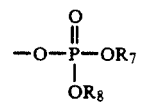

where $R_7$ and $R_8$ have the meanings given above for this preferred set of embodiments. In another preferred embodiment of this preferred set of embodiments $R_1$, $R_2$, $R_3$ and $R_4$ are hydroxyl; and $R_5$ and $R_6$ are

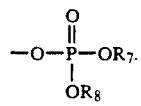

In yet another preferred embodiment of this set of embodiments $R_1$, $R_2$, $R_3$, $R_4$ and $R_5$ are hydroxyl and $R_6$ is

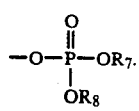

In another series of this preferred set of embodiments the meanings of $R_1$, $R_2$, $R_3$, $R_4$, $R_5$ and $R_6$ are identical. However, in this series the compounds have the structural formula III.

In a third preferred set of embodiments the substituents $R_1$, $R_2$, $R_3$, $R_4$, $R_5$ and $R_6$ are hydroxyl,

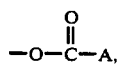

where A has the meanings given for the compound having the structural formula II or

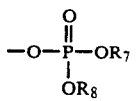

where $R_7$ and $R_8$ are the same or different and are hydrogen, acyloxyalkyl, straight or branched chain alkyl containing 1 to 24 carbon atoms, cycloalkyl containing 3 to 16 carbon atoms or aryl containing 6 to 26 ring carbon atoms.

In this third preferred set of embodiments, one series of compounds has the generic structural formula II. In another series the compounds have the specific structural formula III. Independent of whether the structural formula is II or III, one group of compounds are characterized by $R_1$, $R_2$ and $R_3$ being the same or different and being

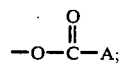

and $R_4$, $R_5$ and $R_6$ being

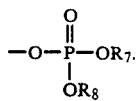

Another preferred group of compounds are defined by $R_1$ and $R_3$ being hydroxyl; $R_2$ being

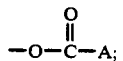

and $R_4$, $R_5$ and $R_6$ being

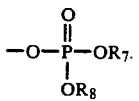

Yet a fourth series of preferred embodiments have the structural formulae II or III where $R_1$, $R_2$, $R_3$, $R_4$, $R_5$ and $R_6$ are hydroxyl; B, as defined in the general definition of the compound having the structural formula II; or

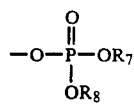

where $R_7$ and $R_8$ are the same or different and are hydrogen, acyloxyalkyl, straight or branched chain alkyl containing 1 to 24 carbon atoms, cycloalkyl containing 3 to 16 carbon atoms or aryl containing 6 to 26 ring carbon atoms.

In one such embodiment of this preferred set of embodiments $R_1$ and $R_3$ are hydroxyl, $R_2$ is B and $R_4$, $R_5$ and $R_6$ are

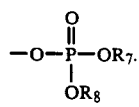

In a second embodiment, $R_1$, $R_3$ and $R_4$ are hydroxyl; $R_2$ is B; and $R_5$ and $R_6$ are

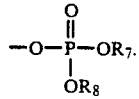

In a third embodiment, $R_1$, $R_3$, $R_4$ and $R_5$ are hydroxyl; $R_2$ is B; and $R_6$ is

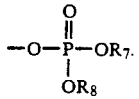

In a fifth series of preferred embodiments the compounds have the structural formula III wherein $R_1$, $R_2$, $R_3$, $R_4$, $R_5$ and $R_6$ being hydroxyl;

where A has the meanings given for A given in the definition of the compound having the structural formula II; or

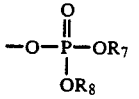

where $R_7$ and $R_8$ are the same or different and are hydrogen, acyloxyalkyl, straight or branched chain alkyl containing 1 to 24 carbon atoms, cycloalkyl containing 3 to 16 carbon atoms or aryl containing 6 to 26 ring carbon atoms.

In one such embodiment $R_1$ and $R_3$ are hydroxyl; $R_2$ is

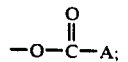

and R4, R5 and R6 are

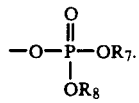

In another embodiment R1, R3 and R4 are hydroxyl; R2 is

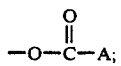

and R5 and R6 are

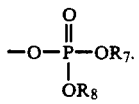

In yet a third embodiment R1, R3, R4 and R5 are hydroxyl; R2 is

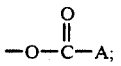

and R6 is

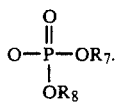

In a preferred embodiment, compounds having the structural formula II are provided wherein R7 is $$R_{10}-\overset{O}{\overset{\|}{C}}-R_{11}-$$

where $R_{10}$ and $R_{11}$ has the meanings given in the definition of the compound having the structural formula II.

In still another preferred embodiment, compounds having the structural formula II are employed wherein R7 is methyl, ethyl, n-propyl, n-butyl, n-pentyl, isopropyl or t-butyl. are used. These compounds are characterized by $R_1$, $R_2$, $R_3$, $R_4$, $R_5$ and $R_6$ having the meanings given for the compounds having the structural formula II.

The described compounds can also exist in dimeric or polymeric forms. The described substituents could per se be e.g. pharmaceutically active compounds. The invention also relates to a composition comprising one or more compounds of Formulae I to III as defined previously.

The composition usually contains 10 to 99.5%, preferably 20 to 99.5% of these compounds.

The invention relates to the above mentioned compounds as pharmaceutically active substances, their use for the manufacture of pharmaceutical preparations and to pharmaceutical preparations containing these compounds.

Of particular importance is the compound having the structural formula

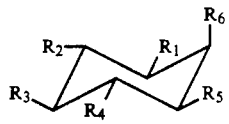 VII where $R_1$, $R_2$ and $R_3$ are the same or different and are
(a) hydroxyl
(b) —O—B where B is
 (1) straight or branched chain alkyl containing 1 to 24 carbon atoms
 (2) cycloalkyl containing 3 to 16 carbon atoms
 (3) alkenyl containing 3 to 24 carbon atoms
 (4) cycloalkenyl containing 5 to 16 carbon atoms
 (5) aryl containing 6 to 26 ring carbon atoms
 (6) aralkyl containing 7 to 48 carbon atoms
 (7) alkaryl containing 7 to 48 carbon atoms
 (8) aralkenyl containing 8 to 48 carbon atoms
 (9) alkenylaryl containing 8 to 48 carbon atoms
 (10) a heterocyclic ring containing at least one atom of oxygen, nitrogen or sulfur
said meaning (1) to (10) of B being unsubstituted or substituted with hydroxy, oxo, alkoxy, aryloxy, halo, cyano, isocyano, carboxy, carbalkoxy, carbaryloxy, amino, alkylsubstituted amino, formyl, acyl, acyloxy, acylamino, sulfinyl, sulfonyl, phosphino, phosphinyl, phosphonyl, mercapto, alkylthio, arylthio, silyl, silyloxy, silylthio, nitro or azido;
 (11) a glycosyl residue
 (12) a glycopeptide
 (13) a glycoprotein
 (14) a glycolipid
 (15) halogen
 (16) carboxy
 (17) carbalkoxy
 (18) carbaryloxy
 (19) sulfonyl
 (20) alkylsubstituted sulfonyl
 (21) arylsubstituted sulfonyl
and where R4, R5 and R6 are the same or different and are

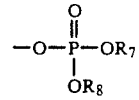

where $R_7$ and $R_8$ are the same or different and are
 (1) hydrogen
 (2) B
 (3) a glycosyl residue
 (4) a glycopeptide
 (5) a glycoprotein
 (6) a glycolipid
 (7) halogen
 (8) carboxy
 (9) phosphonyl
 (10) sulfonyl
 (11) an amino acid
 (12) a peptide
 (13) a protein complex including a lipoprotein and a nucleoprotein
 (14) cyclohexyl
 (15) phosphate substituted cyclohexyl; or
b) hydroxyl, with the proviso that if $R_1$, $R_2$ and $R_3$ are hydroxyl at least one of $R_4$, $R_5$ and $R_7$ is

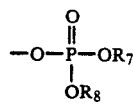

c) —O—B with the proviso that at least one of $R_4$, $R_5$ and $R_6$ is

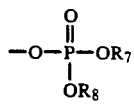

In a first set of embodiments $R_1$, $R_2$ and $R_3$ are —O—B where B is unsubstituted or substituted alkyl, alkenyl, cycloalkyl, cycloalkenyl, aryl, aralkyl, alkaryl, aralkenyl, alkenylaryl, pyranyl, furanyl and silyl. Preferably B is methoxymethyl, methylthiomethyl, benzyloxymethyl, p-metoxybenzyloxymethyl, (4-methoxyphenoxy)methyl, t-butoxymethyl, siloxymethyl, trimethylsiloxymethyl, trichloroethoxymethyl, tetrahydopyranyl, tetrahydrothiopyranyl, tetrahydrofuranyl, tetrahydrothiofuranyl, benzyl, metoxybenzyl, dimetoxybenzyl, dichlorobenzyl, phenylbenzyl, trimethylsilyl, triethysilyl, triisopropylsilyl, t-butyldimethylsilyl, tribenzylsilyl and t-butylmetoxyphenylsilyl.

In this set of embodiments $R_4$, $R_5$ and $R_6$ are

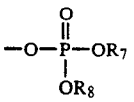

where $R_7$ and $R_8$ are the same or different and are hydrogen, acyloxyalkyl, straight or branched chain alkyl containing 1 to 24 carbon atoms, cycloalkyl containing 3 to 16 carbon atoms or aryl containing 6 to 26 ring carbon atoms.

In a second set of embodiments $R_1$, $R_2$ and $R_3$ and one of $R_4$, $R_5$ and $R_6$ are —O—B where B has the meaning given for the compound having the structural formula VII and the remaining of $R_4$, $R_5$ and $R_6$ are

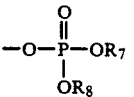

where $R_7$ and $R_8$ are as defined above.

In a third set of embodiments $R_1$, $R_2$ and $R_3$ and two of $R_4$, $R_5$ and $R_6$ are —O—B with B as defined above and the remaining of $R_4$, $R_5$ and $R_6$ is

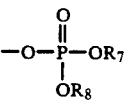

where $R_7$ and $R_8$ are as defined above.

In a fourth set of embodiments one of $R_1$, $R_2$ and $R_3$ is —O—B; the remaining of $R_1$, $R_2$ and $R_3$ are hydroxyl and $R_4$, $R_5$ and $R_6$ are

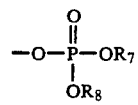

where $R_7$ and $R_8$ are as defined above.

In a fifth set of embodiments one of $R_1$, $R_2$, $R_3$, $R_4$, $R_5$ and $R_6$ is —O—B, two of $R_4$, $R_5$ and $R_6$ are

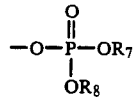

where $R_7$ and $R_8$ are as defined above and the remaining $R_1$, $R_2$, $R_3$, $R_4$, $R_5$ and $R_6$ are hydroxyl.

In a sixth set of embodiments one of $R_1$, $R_2$, $R_3$, $R_4$, $R_5$ and $R_6$ is —O—B, one of $R_4$, $R_5$ and $R_6$ is

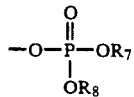

where $R_7$ and $R_8$ are as defined above and the remaining of $R_1$, $R_2$, $R_3$, $R_4$, $R_5$ and $R_6$ are hydroxyl.

The invention relates to the above mentioned compounds as pharmaceutically active substances, their use for the manufacture of pharmaceutical preparations and to pharmaceutical preparations containing these compounds.

The invention also relates to the above mentioned compounds as additives for foodstuffs or stabilizers for different products. The present invention particularly aims at a method of reducing the negative effect of various metal ions, e.g. cadmium, aluminum, lead, mercury, nickel or chromium ions or free radicals in the body tissues. Said method comprises administering to a person or an animal, i.e. mammals, an amount of inventive compounds to interfere with such metal ion or inhibit or reduce the formation of free radicals in the body. The invention also comprises a method of preventing or alleviating one of the following conditions: an arthritic condition, bronchitis, a cell proliferation change, a cancer, high blood pressure, a cardiovascular disease, age diabetes, damage to the placenta, damage to the testicles, damage to different parts of the eye such as retina tissue and lens, damage to the prostate, damage to cell membranes, damage to the central nervous system, damage to the conducting system of the heart, emphysema, lung fibrosis, migraine headache, menstruation disorders, endothelium damage, kidney damage, thrombosis, multiple sclerosis, increased platelet aggregation, inhibition of prostacycline production, metal intoxication, allergy caused by lead, mercury, nickel or chromium, inflammatory conditions, damage to connective tissue, liver damage, brain damage, immunodeficiency, conditions of shock, gastroenteritis, dermatitis and neurological disturbance. Said conditions are attributable to or are caused or aggravated by the presence of metal ions or free radicals in the body.

The method comprises administering to a human or an animal an amount of the inventive compound sufficient to obtain said prevention or alleviation. Furthermore, the invention covers a method of alleviating the detrimental effect of radiation in the body, which method comprises administering to a human or an animal an amount of the inventive compound sufficient to alleviate said radiation effect. For instance, the radiation can be X-ray or nuclear radiation, but other kinds of radiation are also contemplated.

The following examples illustrate the invention but do not restrict it in any way.

EXAMPLE 1

Two hundred μmol of D-myo-inositol-1,2,6-triphosphate in acid form was freeze-dried in a vial. Four hundred mg sodium hydroxide (NaOH) was dissolved in 10 ml dimethylsulphoxide (DMSO) and added to the vial.

Two ml methyliodide was added and the mixture was stirred under dry nitrogen atmosphere for one hour. After neutralization with 1.0 M sodiumhydroxide an excess of calciumchloride was added to give a precipitate of the formed methyleter.

Structural determination with NMR and IR showed the product to be the trimethylether of D-myo-inositol-1,2,6-triphosphate.

EXAMPLE 2

One hundred ml of a solution of the sodiumsalt of myo-inositol-1,2,3-triphosphate with a concentration of 0.05M was added to 100 ml of a mixture of 15% aqueous sodium bisulphate and ethyl alcohol at room temperature. The mixture was neutralized with 1.0M sodiumhydroxide and calciumchloride was added to give a precipitate of the calciumsalt of the formed ethylether.

Structural determination with NMR and IR showed the product to be the triethylether of myo-inositol-1,2,3-triphosphate.

EXAMPLE 3

One hundred μmol of D-myo-inositol-1,2,6-triphosphate in acid form was freeze-dried in a vial. Two hundred mg sodiumhydroxide was dissolved in 5 ml dimethylsulphoxide (DMSO) and added to the vial. Five hundred μl dimethylsulphate was added and the mixture was stirred under dry nitrogen atmosphere for one hour.

After addition of one ml water the mixture was purified via gel chromatography using silica gel.

Structural determination with NMR and IR showed the product to be D-myo-inositol-1,2,6 tri(dimethylphosphate).

EXAMPLE 4

Two ml of a 80% solution of myo-inositol-1,3,4-triphosphate in acid form was added to 4 ml methylene chloride followed by an addition of 2 ml of a diazomethane solution containing excess of diazomethane. After standing at room temperature for 30 minutes the reaction mixture was evaporated to dryness.

Structural determination with NMR and IR showed the product to be myo-inositol-1,3,4 tri(dimethylphosphate).

EXAMPLE 5

Five hundred mg D-myo-inositol-1,2,6-triphosphate in acid form was mixed with five ml acetylchloride-trifluoracetic acid (1:2) at room temperature.

The mixture was sonicated for 60 hrs and then evaporated to dryness.

Structural determination showed the product to be D-3,4,5-tri-O-acetyloxy-myo-inositol-1,2,6-triphosphate.

EXAMPLE 6

Five ml of a 80% solution of D-myo-inositol-1,2,6-triphosphoric acid was added to 10 ml of dodecanoic acid at room temperature.

The mixture was stirred for two hours and then neutralized with 0.1M sodium hydroxide. Six grams of calcium chloride was added to give a precipitate of the calciumsalt of the formed dodecylester. Structural determination with NMR and IR showed the product to be the monododecylester of D-myo-inositol-1,2,6-triphosphate.

EXAMPLE 7

An excess of hydrogenfluoride was added to one hundred mg freeze-dried D-myo-inositol-1,2,6-triphosphate in the presence of one ml concentrated sulphuric acid. After stirring of the mixture for one hour in room temperature the residue was evaporated and purified with HPLC (reversed phase). The purified compound was D-3,4,5-tri-fluoro-myo-inositol-triphosphate.

EXAMPLE 8

Five hundred mg D-myo-inositol-1,2,6-triphosphate in freeze-dried form was mixed with 1.0 ml concentrated sulphuric acid at 0° C. for 30 min.

Excess of sulphuric acid was removed by gelchromatography and the resulting purified compound was shown to be D-3,4,5-trisulpho-myo-inositol-1,2,6-triphosphate.

EXAMPLE 9

To two hundred mg of the sodiumsalt of D-myo-inositol-1,2,6-triphosphate was added five ml 5.0M sodium hydroxide in a closed vial. Excess of carbon disulfide was introduced and maintained at 40° C. for three hrs under stirring. The mixture was evaporated and the resulting compound was identified as the xanthate ester of D-myo-inositol-1,2,6-triphosphate.

EXAMPLE 10

One hundred μmol of D-myo-inositol-1,2,6-triphosphate was mixed with 600 mg sodiumhydroxide in two ml water. To this solution 550 mg sodiumchloracetate was added and the reaction mixture was heated to 70° C. for 5 hrs. After cooling to room temperature the mixture was neutralized with 2.0M hydrochloric acid and calcium chloride was added to give a precipitate, which was shown to be D-3,4,5-tri-O-carboxy-myo-inositol-1,2,6-triphosphate.

EXAMPLE 11

0.5 g of the tetrabutylammoniumsalt of D-myo-inositol-1,2,6-triphosphate was dissolved in dichloromethane. To this solution 0.2 g of pyridinium chlorochromate was added and the mixture was stirred for 48 hrs at 25° C. The reaction mixture was filtered through silica gel and the purified compound was determined to be D-4-oxy-myo-inositol-1,2,6-triphosphate.

EXAMPLE 12

A solution of (benzyloxymethyl)tributylstannane (0.7 g) in tetrahydrofuran was cooled to −78° C. under a nitrogen atmosphere and n-butyllithium (1.0 ml 1.6M in hexane) was added.

After 20 minutes at −78° C. 0.5 g of the compound formed in example 11, D-4-oxy-myo-inositol-1,2,6-triphosphate in tetrahydrofuran (2 ml) was added. After 30 minutes the reaction mixture was partitioned between diethylether and water. The organic phase was dried with sodium sulphate and evaporated. The residue was purified by HPLC and was shown to be D-4-C-benzyloxymethyl-myo-inositol-1,2,6-triphosphate.

EXAMPLE 13

0.6 g of the compound formed in example 11, D-4-oxy-myo-inositol-1,2,6-triphosphate was dissolved in 10 ml water and hydroxylamine hydrochloride (110 mg) and an aqueous solution of sodium acetate (100 mg in 5 ml water) was added dropwise under stirring. The mixture was stirred further for 2.5 hours at room temperature.

To the reaction mixture 5% sodium amalgam (total 20 g) was added at 5 min intervals for one hour under stirring and cooling to below 25° C. in a water bath. After removal of mercury by decantation the supernatant was purified with ion-exchange chromatography.

Structural determination showed the product to be D-4-amino-myo-inositol-1,2,6-triphosphate.

EXAMPLE 14

Five ml of a 80% solution of D-myo-inositol-1,2,6-triphosphate in acid form was added to the cesium salt of glycine (2.5 g) and further 1.0 ml of concentrated sulphuric acid was added. The mixture was stirred for two hours in room temperature and then neutralized with 1.0M NaOH. Six grams of calcium chloride was added to give a precipitate which was shown to be the monoglycyl ester of D-myo-inositol-1,2,6-triphosphate.

EXAMPLE 15

1.0 g of the tetrabutylammoniumsalt of D-myo-inositol-1,2,6-triphosphate was dissolved in chloroform. Galactose (850 mg) and anhydrous hydrogen chloride (1.0 ml) was added and the mixture was heated under reflux for 12 hours.

After cooling to room temperature the mixture was purified with gelchromatography (silica gel) and a compound determined by NMR to be 4-O-galactosyl-myo-inositol-1,2,6-triphosphate was isolated.

EXAMPLE 16

One hundred mg of D-myo-inositol-1,2,6-triphosphate was freeze-dried in a vial. One ml of N,O-bis(trimethylsilyl)trifluroacetamide-chlorotrimethylsilane-pyridine (9:9:10;v:v:v) was added and taken to dryness under a stream of nitrogen and then dissolved in 1.0 ml of 10% anhydrous methanol in diethyl ether at 0° C. After 15 minutes the mixture was evaporated and structural determination of the residue showed it to be D-3,4,5-tri-O-trimethylsilyl-myo-inositol-1,2,6-triphosphate.

EXAMPLE 17

The silver salt of myo-inositol-2-mono-phosphate was obtained from the corresponding sodium salt by reaction with silver nitrate in water.

0.5 g of the silver salt was suspended in 20 ml of toluene and a 2 molar excess of iodomethyl pivaloate was added. The reaction was continued for 6 hours at room temperature and after filtration the toluene phase was chromatographed on a semi-preparative $C_{18}$-column. Two different peaks were obtained which were investigated with NMR.

The first peak consisted of the monosubstituted pivaloyloxymethyl-inositol-2-monophosphate, while the second peak was the bis(pivaloyloxymethyl)inositol-mono-2-phosphate at a yield of 37%.

EXAMPLE 18

A silver salt of D-myo-inositol-1.2.6-triphosphate was obtained from the corresponding compound in acid form by adding silver nitrate and by raising the pH to 8.

0.8 g of the silver salt was suspended in 30 ml of acetonitrile and a 2.5 molar excess of iodomethyl acetate was added. The reaction was continued for 8 hours at 30° C. After filtration the reaction mixture was loaded on a semi-preparative $C_{18}$-column and eluted with acetonitrile/water=80/20 (by volume). The different fractions were investigated by NMR. One fraction with a yield of 46% was found to be hexakis-(acetoxymethyl)-myo-inositol-1.2.6-trisphosphate.

EXAMPLE 19

1.00 g of the silver salt of D-myo-inositol-1.2.6-trisphosphate was mixed with 3.88 ml n-butyl-iodide in 20 ml dimethylformamide (DMF). The reaction mixture was heated to 65° C. for 18 hours with continuous stirring.

After the reaction the DMF was removed by distillation and the remaining mixture was extracted with methylene chloride. This phase was evaporated and dried in vacuum. NMR on the residue proved the product to be hexakisbutyl-myo-inositol-1.2.6-trisphosphate.

EXAMPLE 20

0.54 g of a sodium salt of D-myo-inositol-1.2.6-trisphosphate was mixed with 10 ml trifluoroacetic acid. To this suspension 7.6 ml benzoyl bromide was added and the reaction mixture was mixed in room temperature for 20 hours.

The reaction mixture was evaporated at reduced pressure in a nitrogen containing atmosphere. After evaporation and cooling to 0° C. sodium hydrogen carbonate was added in order to neutralize the compound found.

After drying the compound was investigated with NMR. The structural determination showed the product to be D-3.4.5-tri-O-benzoyloxy-myo-inositol-1.2.6-trisphosphate.

EXAMPLE 21

0.66 g of the acid form of D-myo-inositol-1.2.3-trisphosphate (IP$_3$) was dissolved in 20 ml dry dimethylformamide (DMF) followed by the addition of 1.57 g succinic acid anhydride and 0.77 g dimethylaminopyridine. The mixture was heated to 60° C. for 90 mins. The DMF was removed by distillation and the remaining residue was extracted in methylene chloride.

After evaporation the structure of the compound was determined to be a derivative of D-myo-inositol-1.2.3-trisphosphate where the hydroxyl groups on the inositol ring were completely substituted with succinic acid groups.

EXAMPLE 22

A mixture of myo-inositol (50 g), dry methyl sulphoxide (160 ml), 2,2-dimethoxypropane (185 ml) and toluene-p-sulphonic acid monohydrate (500 mg) was stirred at 100° C. for 1 hour. Triethylamine (10 ml) was added to the cooled solution and the solvent was evaporated. The products were extracted with dichloromethane.

The extract was shown to contain a mixture of di-O-isopropylidene derivatives of myo-inositol, i.e. 1,2:3,4-di-O-isopropylidene-myo-inositol, 1,2:4,5-di-O-isopropylidene-myo-inositol and 1,2:5,6-di-O-isopropylidene-myo-inositol.

The mixture of di-O-isopropylidene derivatives were treated with a 20% molar excess of benzoyl chloride in pyridine in order to form the corresponding benzoates. The precipitated material was filtered off while the soluble benzoates were triturated with boiling light petroleum. After recrystallization from methanol 28 g of 1,2:5,6-di-O-isopropylidene-3,4-di-O-benzoyl-myo-inositol was formed.

The benzoate was hydrolysed with sodium hydroxide in methanol and formed 12.4 g of the racemic 1,2:5,6-di-O-isopropylidene-myo-inositol. This compound was treated with a 40% molar excess of allylbromide and sodium hydroxide in N,N-di-methylformamide at 20° C. for 3 hours and the isolated product was 1,2:5,6-di-O-isopropylidene-3,4-di-O-allyl-myo-inositol (14.4 g).

This substance was partially hydrolysed with 1.5 g toluene-p-sulphonic acid monohydrate in 200 ml acetone and 5 ml water at 20° C. for 45 minutes. Triethylamine (10 ml) and sodium hydrogen carbonate (3 g) was added and the solvents were evaporated off. The residue was triturated with ether (500 ml) and filtered. The unsoluble material was identified with NMR to be 1,2-O-isopropylidene-3,4-di-allyl-myo-inositol (12.2 g).

9.5 g of this compound was treated with a 30% molar excess of benzyl bromide and sodium hydride in N,N-dimethylformamide and the corresponding dibenzylether, i.e. 1,2-di-O-isopropylidene-3,4-di-O-allyl-5,6-di-O-benzyl-myo-inositol was isolated (13.6 g). Hydrolysis was performed by heating in acetic acid/water (4:1) at reflux for 30 mins.

The formed substance, 3,4-di-O-allyl-5,6-di-O-benzyl-myo-inositol (12.1 g) together with dibutylin oxide (4.0 g) and dry benzene (150 ml) was heated under reflux for 2 hours. After evaporation of benzene and addition of dry dimethyl formamide (60 ml) and benzyl bromide (5.5 ml) the solution was kept at 50° C. for 24 hours. The crude product was chromatographed on silica gel (250 g) and eluted with ether-light petroleum to give 9.5 g of 1,5,6-tri-O-benzyl-3,4-di-O-allyl-myo-inositol. A mixture of the obtained product, toluene-p-sulphonic acid monohydrate (0.9 g), ethanol (190 ml), water (10 ml) and palladium-on-charcoal (1 g, 10% from Fluka) was heated under reflux with stirring for 4 hours. The crude product was chromatographed on silica gel and elution with ether-light petroleum (4:1) gave a compound, identified with NMR to be 1,5,6-tri-O-benzyl-myo-inositol. The described substances are racemic mixtures. If desired the racemic mixture of the latter one could be separated into the enantiomeric forms by forming diastereomers with camphanic acid.

500 mg of (+) 1,5,6-tri-O-benzyl-myo-inositol was mixed with 3.0 g 2-cyanoethyl N,N-diisopropyl-phosphoramidochloridite in 20 ml dichloromethane. Treatment with tetrazole and 2.0 ml 2-cyanoethanol was followed by oxidation with 50 mg t-butylhydroperoxide for 20 mins. The resulting compound was exposed to liquid ammonia for 3 hrs at 60° C. for removal of the 2-cyanoethyl groups. With NMR the identification of 3,4,5-tri-O-benzyl-1,2,6-trisphosphate was made.

We claim:
1. An ether of myo-inositol phosphate having the structural formula

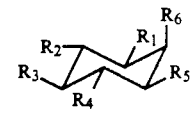

where $R_1$, $R_2$ and $R_3$ are the same or different and are
a(/)) hydroxyl
b(/)) —O—B where B is
  (1) straight or branched chain alkyl containing 1 to 24 carbon atoms,
  (2) cycloalkyl containing 3 to 16 carbon atoms,
  (3) alkenyl containing 3 to 24 carbon atoms,
  (4) cycloalkenyl containing 5 to 16 carbon atoms,
  (5) aryl containing 6 to 24 ring carbon atoms,
  (6) aralkyl containing 7 to 48 carbon atoms,
  (7) alkaryl containing 7 to 48 carbon atoms,
  (8) aralkenyl containing 8 to 48 carbon atoms,
  (9) alkenylaryl containing 8 to 48 carbon atoms,
  (10) a heterocyclic ring containing at least one atom of oxygen, nitrogen or sulfur
  said meanings (1) to (10) of B being unsubstituted or substituted with hydroxy, oxo, alkoxy, aryloxy, halo, cyano, isocyano, carboxy, carbalkoxy, carbaryloxy, amino, alkyl-substituted amino, formyl, acyl, acyloxy, acylamino, sulfinyl, sulfonyl, phosphino, phosphinyl, phosphonyl, mercapto, alkylthio, arylthio, silyl, silyloxy, silylthio, nitro or azido
  (11) a glycosyl residue
  (12) a glycopeptide
  (13) a glycoprotein
  (14) a glycolipid
  (15) halogen
  (16) carboxy
  (17) carbalkoxy
  (18) carbaryloxy
  (19) sulfonyl
  (20) alkyl-substituted sulfonyl
  (21) aryl-substituted sulfonyl
and where $R_4$, $R_5$ and $R_6$ are the same or different and are

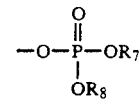    a)

where $R_7$ and $R_8$ are the same or different and are
(1) hydrogen
(2) B
(3) a glycosyl residue
(4) a glycopeptide
(5) a glycoprotein
(6) a glycolipid
(7) halogen
(8) carboxy
(9) phosphonyl
(10) sulfonyl
(11) an amino acid
(12) a peptide
(13) a protein complex including a lipoprotein and a nucleoprotein
(14) cyclohexyl
(15) phosphate substituted cyclohexyl; or
b) hydroxyl or c) —O—B with the provisos that at least one of $R_4$, $R_5$ and $R_6$ is

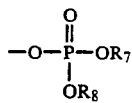

and that at least one of $R_1$, $R_2$, $R_3$, $R_4$, $R_5$, and $R_6$ is —O—B.

2. An ether in accordance with claim 1 wherein $R_1$, $R_2$ and $R_3$ are —O—B; and where $R_4$, $R_5$ and $R_6$ are

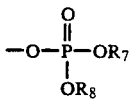

where $R_7$ and $R_8$ are the same or different and are hydrogen, acyloxyalkyl, straight or branched chain alkyl containing 1 to 24 carbon atoms, cycloalkyl containing 3 to 16 carbon atoms or aryl containing 6 to 24 ring carbon atoms.

3. An ether in accordance with claim 2 wherein $R_1$, $R_2$ and $R_3$ are methoxymethyl, benzyl or tetrahydropyranyl and wherein $R_4$, $R_5$ and $R_6$ are

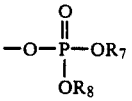

where $R_7$ and $R_8$ are hydrogen.

4. An ether in accordance with claim 1 wherein $R_1$, $R_2$ and $R_3$ and one of $R_4$, $R_5$ and $R_6$ are —O—B; and where the remaining of $R_4$, $R_5$ and $R_6$ are

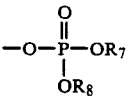

where $R_7$ and $R_8$ are the same or different and are hydrogen, acyloxyalkyl, straight or branched chain alkyl containing 1 to 24 carbon atoms, cycloalkyl containing 3 to 16 carbon atoms or aryl containing 6 to 24 ring carbon atoms.

5. An ether in accordance with claim 1 wherein $R_1$, $R_2$, $R_3$ and the two of $R_4$, $R_5$ and $R_6$ are —O—B; and where the remaining of $R_4$, $R_5$ and $R_6$ is

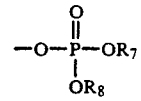

where $R_7$ and $R_8$ are the same or different and are hydrogen, acyloxyalkyl, straight or branched chain alkyl containing 1 to 24 carbon atoms, cycloalkyl containing 3 to 16 carbon atoms or aryl containing 6 to 24 ring carbon atoms.

6. An ether in accordance with claim 1 wherein one of $R_1$, $R_2$ and $R_3$ is —O—B; where the remaining of $R_1$, $R_2$ and $R_3$ are hydroxyl and where $R_4$, $R_5$ and $R_6$ are

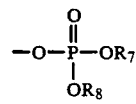

where $R_7$ and $R_8$ are the same or different and are hydrogen, acyloxyalkyl, straight or branched chain alkyl containing 1 to 24 carbon atoms, cycloalkyl containing 3 to 16 carbon atoms or aryl containing 6 to 24 ring carbon atoms.

7. An ether in accordance with claim 1 wherein one of $R_1$, $R_2$, $R_3$, $R_4$, $R_5$ and $R_6$ is —O—B; where two of $R_4$, $R_5$ and $R_6$ are

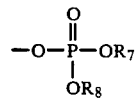

where $R_7$ and $R_8$ are the same or different and are hydrogen, acyloxyalkyl, straight or branched chain alkyl containing 1 to 24 carbon atoms, cycloalkyl containing 3 to 16 carbon atoms or aryl containing 6 to 24 ring carbon atoms and where the remaining of $R_1$, $R_2$, $R_3$, $R_4$, $R_5$ and $R_6$ are hydroxyl.

8. An ether in accordance with claim 1 wherein one of $R_1$, $R_2$, $R_3$, $R_4$, $R_5$ and $R_6$ is —O—B; where one of $R_4$, $R_5$ and $R_6$ is

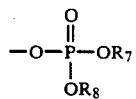

where $R_7$ and $R_8$ are the same or different and are hydrogen, acyloxyalkyl, straight or branched chain alkyl containing 1 to 24 carbon atoms, cycloalkyl containing 3 to 16 carbon atoms or aryl containing 6 to 24 ring carbon atoms and where the remaining of $R_1$, $R_2$, $R_3$, $R_4$, $R_5$ and $R_6$ are hydroxyl.

9. An ether in accordance with claim 1 where B is methoxymethyl, benzyloxymethyl, p-methoxybenzyloxymethyl, t-butoxymethyl, siloxymethyl, trimethylsiloxymethyl, tetrahydropyranyl, tetrahydrofuranyl, benzyl, metoxybenzyl, phenylbenzyl, trimethylsilyl, tribenzylsilyl and triphenylsilyl.

* * * * *